(12) United States Patent
Kasahara et al.

(10) Patent No.: US 10,660,990 B2
(45) Date of Patent: May 26, 2020

(54) ARTICLE WITH FOAMED SURFACE, IMPLANT AND METHOD OF PRODUCING THE SAME

(71) Applicant: NGK SPARK PLUG CO., LTD., Nagoya-shi, Aichi (JP)

(72) Inventors: Shinjiro Kasahara, Nagoya (JP); Takenori Sawamura, Nagoya (JP)

(73) Assignee: NGK SPARK PLUG CO., LTD., Aichi (JP)

(*) Notice: Subject to any disclaimer, the term of this patent is extended or adjusted under 35 U.S.C. 154(b) by 331 days.

(21) Appl. No.: 15/870,274

(22) Filed: Jan. 12, 2018

(65) Prior Publication Data

US 2018/0200410 A1    Jul. 19, 2018

Related U.S. Application Data

(63) Continuation of application No. 12/864,781, filed as application No. PCT/JP2008/002717 on Sep. 29, 2008, now Pat. No. 9,931,438.

(30) Foreign Application Priority Data

Jan. 28, 2008  (JP) ................................. 2008-016780

(51) Int. Cl.
*A61L 27/56*       (2006.01)
*A61L 27/14*       (2006.01)
(Continued)

(52) U.S. Cl.
CPC ............... *A61L 27/56* (2013.01); *A61L 27/14* (2013.01); *A61L 27/18* (2013.01); *A61L 27/44* (2013.01)

(58) Field of Classification Search
CPC ...................................................... A61L 27/56
See application file for complete search history.

(56) References Cited

U.S. PATENT DOCUMENTS

| 4,164,794 | A | * | 8/1979 | Spector | ............... | A61C 8/0012 |
| | | | | | | 427/195 |
| 4,351,069 | A | * | 9/1982 | Ballintyn | ............ | A61C 8/0016 |
| | | | | | | 623/23.36 |

(Continued)

FOREIGN PATENT DOCUMENTS

| EP | 0 269 256 A1 | 6/1988 |
| EP | 0 610 953 A1 | 2/1994 |

(Continued)

OTHER PUBLICATIONS

Japanese Patent Office, "First Notification of Reasons for Rejection," issued in connection with Japanese Patent Application No. 2009-551322, dated Dec. 7, 2012.

(Continued)

*Primary Examiner* — Cachet I Proctor
(74) *Attorney, Agent, or Firm* — Sughrue Mion, PLLC

(57) ABSTRACT

A method of producing an article with a foamed surface which includes: a step 1 of forming small pores in a surface of a base made of a plastic to produce a base with small pores; a step 2 of immersing the base with small pores, obtained in step 1, in a solution including a foaming agent to prepare a foaming agent-including base; a step 3 of immersing the foaming agent-including base, obtained in step 2, in a foaming solution that makes the plastic swell and the foaming agent foam to prepare a foamed base; and a step 4 of immersing the foamed base, obtained in step 3, in a coagulating solution that coagulates the swollen plastic.

12 Claims, 12 Drawing Sheets

(51) Int. Cl.
  *A61L 27/18* (2006.01)
  *A61L 27/44* (2006.01)

(56) References Cited

U.S. PATENT DOCUMENTS

| | | | |
|---|---|---|---|
| 6,551,355 B1* | 4/2003 | Lewandrowski | A61L 27/34 623/16.11 |
| 6,602,293 B1* | 8/2003 | Biermann | A61F 2/30965 623/23.5 |
| 2004/0210316 A1 | 10/2004 | King et al. | |
| 2005/0019365 A1 | 1/2005 | Frauchiger et al. | |
| 2005/0112397 A1 | 5/2005 | Rolfe et al. | |
| 2005/0169956 A1 | 8/2005 | Erbe et al. | |
| 2007/0111165 A1* | 5/2007 | Wallick | C08L 71/00 433/212.1 |
| 2007/0191962 A1 | 8/2007 | Jones et al. | |
| 2010/0004753 A1* | 1/2010 | Lerf | A61L 27/306 623/18.11 |

FOREIGN PATENT DOCUMENTS

| | | |
|---|---|---|
| JP | 25425 B2 | 2/1990 |
| JP | 420353 B2 | 4/1992 |
| JP | 6322168 A | 11/1994 |
| JP | 2001504008 A | 3/2001 |
| JP | 2002146086 A | 5/2002 |
| JP | 2002522157 A | 7/2002 |
| JP | 2003210569 A | 7/2003 |
| JP | 2004313794 A | 11/2004 |
| JP | 2006158953 A | 6/2006 |
| JP | 2006528515 A | 12/2006 |
| WO | 1998019617 A1 | 5/1998 |
| WO | 200009043 A1 | 2/2000 |
| WO | 0200275 A1 | 1/2002 |
| WO | 2007051307 A2 | 5/2007 |
| WO | 2007051519 A2 | 5/2007 |

OTHER PUBLICATIONS

Supplementary European Search Report issued in PCT/JP2008/002717 dated Mar. 13, 2013.
Vaidyanathan, et al., "Restorable polymer-ceramic composites for orthopedic scaffold applications," Database CA, XP002692795, STN, Accession No. 2004:1075070.
Perman et al., Thermoplastic Foam Article and its Preparation, Nov. 22, 1994, machine translation of JP6322168A.
Inoue et al., Porous Bone Augmentation Material, Jul. 29, 2003, machine translation of JP2003-210569A.

* cited by examiner

ARTICLE WITH FOAMED SURFACE, IMPLANT AND METHOD OF PRODUCING THE SAME

This application is a continuation of U.S. application Ser. No. 12/864,781, filed Sep. 20, 2010 which is a national stage entry of PCT/JP2008/002717, filed Sep. 29, 2008, which claims benefit to Japanese Patent Application No. 2008-016780, filed Jan. 28, 2008, the entire contents of each of which is incorporated herein by reference.

TECHNICAL FIELD

The present invention relates to an article with a foamed surface, an implant and a method of producing them. More particularly the present invention relates to an article with a foamed surface which shows mechanical properties similar to those of bone or teeth when applied especially to an implant, and has a surface structure into which bone tissue easily penetrated when implanted in the body of a living organism; an implant; and a method of producing them.

BACKGROUND ART

When a large part of bone is lost, employed as a medical treatment is bone autotransplantation in which apiece of bone is removed from a patient's own normal bone and grafted into the bone defect, or artificial bone implantation in which a piece of artificial bone made of an artificial material is implanted into the defect. However, a limited amount of harvested bone imposes limitations on bone autotransplantation. Besides, bone autotransplantation falls heavily on the body of the patient because normal cells are damaged during surgery. In addition, because the removal of apiece of bone to be utilized for autologous bone grafting from a patient's own normal bone creates a new defect in the bone, this method cannot be an essential treatment when the amount of missing bone is large. On the other hand, artificial bone implantation does not have problems that bone autotransplantation has, because the former employs industrially manufactured artificial bone. However the mechanical and biological properties of artificial bone are different from those of natural bone, the properties of an artificial bone place limitations on the use thereof. For example, artificial bone made of metal materials such as titanium alloy, which normally have high strength while having a large coefficient of elasticity and lacking toughness, causes stress shielding due to differences in mechanical properties between the metal material and the surrounding bone, when the artificial bone is implanted in parts that are continuously under great load. Another problem of artificial bone is that it is not directly integrated into natural bone. On the other hand, artificial bone made of bioceramics such as hydroxyapatite, is usually highly biocompatible as well as highly bioactive and excellent in binding with natural bone, while it is weak against external impact. Thus it is not suitable to use at parts or places that tend to receive large load in a moment.

The selection of polymers such as ultra high molecular weight polyethylene for a material of artificial bone solves the problems that metal materials and bioceramics have. In particular, polyetheretherketone, which is often abbreviated to PEEK, has mechanical properties close to the mechanical properties of natural bone, and PEEK is also excellent in biocompatibility. Therefore its adaptation to orthopedic materials used at parts that require high strength is expected. Furthermore, artificial bone made of a combined material of polymer and bioceramics with biological activity, capable of directly binding with the native bone, has been developed.

On the other hand, it is well known that the structure of artificial bone, as well as chemical properties such as biocompatibility and biological activity and physical properties such as strength and elastic modulus, is an important factor from the viewpoint of binding capability with the native bone. Developed are many artificial bones whose surface or entire structure is made porous to facilitate penetration of the biological tissue into the inside thereof when it is implanted in the body of a living organism. Innovative approaches to providing artificial bone made of polymeric materials including PEEK with a porous superficial layer or a convexo-concave surface have been made in order to make the best use of its strength and to make it have binding capability with native bone.

Patent document 1 discloses an artificial acetabular cup including a lining layer, which has a porous structure made by sputtering PEEK particles with a plasma torch, against a bearing superficial layer made of a composite material of PEEK and carbon short fibers.

Patent document 2 teaches a sponge-like structure formed by a plurality of polymer sheets each with at least one aperture wherein the polymer sheets are stacked up and stuck together with the locations of the apertures shifted with each other.

Patent document 3 discloses an orthopedic tool, capable of being implanted, having a porous organic polymer layer with desired pores. The method of forming the porous organic polymer layer comprises embedding a pore-forming agent in a polymeric material, allowing the organic polymer to contact a solvent for eluting the pore-forming agent in order to make the solvent to elute the agent and form desired pores.

Patent document 4 teaches an orthopedic implant formed from a thermoplastic resin with a convexo-concave surface wherein the convexities and concavities are formed by etching, sand blasting, grinding or other methods.

Patent document 5 discloses a method of heat molding a thermoplastic material with a mold having concavities and convexities in the inner walls thereof.

Patent document 6 teaches a method of decalcomania transferring of concavities and convexities in the surface of a surgical implant comprising press-fitting an acid-soluble metal plate with a predetermined shape into the surface of the surgical implant made of a thermoplastic resin, and dissolving the acid-soluble plate.

However, the conventional methods and products have defects: Some require expensive apparatuses, like the product of patent document 1; others call for sheet materials to form a porous structure in addition to a polymeric material for parenchyma to realize the strength of artificial bone, like the product of patent document 2; or still others need preparation of polymers including a pore-forming agent, like the product of patent document 3. It is easily supposed that the method of patent document 4 does not provide sufficient concavities and convexities suitable to let biological tissue penetrate into the implant. Furthermore, the methods taught in patent documents 5 and 6 are not suitable to form a porous structure in the surface of polymeric material with a complicated shape.

Also known are methods of making a polymeric material foam thereby forming a porous structure. Among them, one well-known method includes steps of dispersing a solvent with a low boiling point as a foaming agent in a high-molecular weight compound, and heating the high-molecular weight compound with the low-boiling-point solvent dispersed therein to volatilize or decompose the solvent and then to generate gas, thereby forming a lot of foam inside the high-molecular weight compound.

Patent document 7 teaches another method including steps of dissolving an inert gas, such as nitrogen gas or carbon dioxide gas, in a thermoplastic resin under a high pressure; releasing the pressure; and heating the thermoplastic resin to a temperature close to its glass transition temperature, thereby making the gas dissolved in the thermoplastic resin foam to produce a porous material.

As understood, all of the aforementioned methods are those to make a high-molecular weight compound in its entirety a porous structure. Such a porous structure includes pores dispersed all over the structure, which may lower the strength thereof depending on the diameters of the pores and the porosity. Therefore the methods are not suitable to produce implants to be used at parts that require high strength.

Patent document 1: JP 2006-158953 A
Patent document 2: JP 2006-528515 T
Patent document 3: JP 2004-313794 A
Patent document 4: JP 2001-504008 T
Patent document 5: JP H2(1990)-5425 B
Patent document 6: JP H4(1992)-20353 B
Patent document 7: JP H6(1994)-322168 A

DISCLOSURE OF THE INVENTION

Problems to be Solved by the Invention

A first objective of the present invention is to provide an article with a foamed surface comprising a plastic base with a porous structure in the surface thereof, the article showing mechanical properties similar to those of bone or teeth when applied especially to an implant, and having a surface structure into which bone tissue easily penetrates when implanted in a biological body. The present invention also provides an implant.

A second objective of the present invention is to provide a method of producing an article with a foamed surface and an implant, capable of producing an article with a foamed surface and an implant with a complicated shape in simple steps.

Means to Solve the Problems

As means to achieve the first objective the present invention provides:

(1) An article with a foamed surface comprising a body and a superficial layer formed in a surface of the body, the superficial layer including small pores with small diameters and large pores with large diameters, wherein the article is made of a plastic, a part of the small and large pores are open pores which are formed in the surface of the superficial layer and are open to the outside, the open pores comprise small open pores with an average diameter of 5 μm or less and large open pores with an average diameter from 10 to 200 μm, and the large open pores that are in the surface of the superficial layer have an inner wall with passages connected with the small pores and the large pores;

(2) The article with the foamed surface as described under item (1), as a preferable embodiment of the article thereof, wherein the article is applied to an implant;

(3) The article with the foamed surface as described under item (1) or (2), wherein the plastic is an engineering plastic;

(4) The article with the foamed surface as described under any one of items (1)-(3), wherein the plastic is polyetheretherketone;

(5) The article with the foamed surface as described under any one of items (1)-(4), wherein the plastic includes at least one fiber selected from the group consisting of carbon fiber, glass fiber, ceramic fiber, metal fiber and organic fiber; and (6) An implant comprising the article with the foamed surface as described in any one of items (1)-(5), and a bioactive substance on the inner wall of the open pores in the superficial layer of the article and/or on the surface thereof.

As means to achieve the second objective the present invention provides:

(7) A method of producing an article with a foamed surface including:
step 1 of forming small pores in a surface of a base made of a plastic to produce a base with small pores;
step 2 of immersing the base with small pores, obtained in step 1, in a solution including a foaming agent to prepare a foaming agent-including base;
step 3 of immersing the foaming agent-including base, obtained in step 2, in a foaming solution that makes the plastic swell and the foaming agent foam to prepare a foamed base; and
step 4 of immersing the foamed base, obtained in step 3, in a coagulating solution that coagulates the swollen plastic.

(8) The method as described under item (7), as a preferable embodiment thereof, further comprising applying the article with the foamed surface to an implant.

(9) The method as described under item (7) or (8), wherein the plastic is an engineering plastic;

(10) The method as described under any one of items (7)-(9), wherein the plastic is polyetheretherketone;

(11) The method as described under any one of items (7)-(10), wherein the plastic includes at least one fiber selected from the group consisting of carbon fiber, glass fiber, ceramic fiber, metal fiber and organic fiber;

(12) The method as described under any one of items (7)-(11), wherein the foaming solution used in step 3 is concentrated sulfuric acid;

(13) The method as described under any one of items (7)-(12), wherein a porous structure formed in a superficial layer of the foamed article is controlled by changing at least one of a kind of the coagulating solution, a concentration of the coagulating solution and a time period for which the foamed base is immersed in the coagulating solution;

(14) The method as described under any one of items (7)-(13), wherein the coagulating solution is at least one selected from the group consisting of water and a slow coagulating solution which takes a longer time to coagulate the swollen plastic than water;

(15) The method as described under any one of items (7)-(14), wherein the slow coagulating solution is a solution of sulfuric acid whose concentration is less than 90%;

(16) The method as described under any one of items (7)-(15), wherein the foaming agent is a carbonate;

(17) The method as described under any one of items (7)-(16), wherein the carbonate includes at least one carbonate compound selected from the group consisting of sodium hydrogen carbonate, sodium carbonate and potassium carbonate; and

(18) A method of producing an implant comprising immersing an article with a foamed surface prepared by the method as described in any one of items (7)-(17) both in a first solution including calcium ions and a second solution including phosphate ions wherein the article may be first immersed in either of the first and second solutions.

Advantages of the Invention

The article with the foamed surface of the present invention is an article comprising a body and a superficial layer formed in a surface of the body, the superficial layer including small pores with small diameters and large pores with large diameters, wherein the article is made of a plastic, a part of the small and large pores are open pores which are formed in the surface of the superficial layer and are open to the outside, the open pores include small open pores with an average diameter of 5 µm or less and large open pores with an average diameter from 10 to 200 µm, and the large open pores that are in the surface of the superficial layer have an inner wall with passages connected with the small pores and the large pores. When this surface foamed article is applied to an implant, the article with the foamed surface of the present invention, which has many open pores that are open to the outside in the surface of the superficial layer and passages connecting these open pores with the small and large pores formed inside the superficial layer, is capable of letting native bone tissue penetrate into the inside of the superficial layer after the article is implanted in the body of a living organism. As a result, new natural bone is formed so that spaces existing in the inside of the superficial layer are filled, which new natural bone makes it possible to integrate the article into the native bone. Furthermore, the article with the foamed surface of the present invention does not have pores all through the volume, but have many pores in the surface thereof, which makes the article to have a strength suitable for a part in which it is implanted.

For the material of this article with a foamed surface, desirable is an engineering plastic, more desirable polyetheretherketone, most desirable a plastic including at least one fiber selected from the group consisting of carbon fiber, glass fiber, ceramic fiber, metal fiber and organic fiber. The employment of these materials will provide the article with high strength. When this article is applied to an implant, the implant will have mechanical properties similar to those of bone or teeth. Therefore this article with the foamed surface, when it is implanted as artificial bone in parts which require integration with the native bone and continuously bear large load, provides a high-strength implant without stress shielding, or possible reduction in the amount of bone and decrease in the density thereof, caused by shielding of stress applied to bone.

When the article with a foamed surface has a bioactive substance on the inner walls of open pores in the superficial layer thereof and/or on the surface of the superficial layer, a chemical reaction takes place between the bioactive substance and bone tissue of the living organism, which expedites formation of new natural bone and results in a quick integration of the implant with the native bone.

The method of producing an article with a foamed surface according to the present invention has step 1 of forming small pores in a surface of a base made of a plastic to produce a base with small pores; step 2 of immersing the base with small pores, obtained in step 1, in a solution including a foaming agent to prepare a foaming agent-including base; step 3 of immersing the foaming agent-including base, obtained in step 2, in a foaming solution that makes the plastic swell and the foaming agent foam to prepare a foamed base; and step 4 of immersing the foamed base, obtained in step 3, in a coagulating solution that coagulates the swollen plastic. Almost all the steps are thus carried out in a liquid phase. Therefore the method does not require special apparatuses and it is capable of easily producing articles with a foamed surface that even have a complicated shape.

For the material of the base, desirable is an engineering plastic, more desirable polyetheretherketone, most desirable a plastic including at least one fiber selected from the group consisting of carbon fiber, glass fiber, ceramic fiber, metal fiber and organic fiber. The employment of these materials for the base will facilitate the production of a surface foamed article with high strength.

Also noticeable is that only changing at least one element selected from the group consisting of a kind of the coagulating solution, a concentration of the coagulating solution and a time period for which the foamed base is immersed in the coagulating solution leads to the production of an article with a foamed surface whose superficial layer has a controlled and desired porous structure.

The method of producing an implant according to the present invention is essentially the same as that of an article with a foamed surface as explained hereinbefore because the former utilizes an article with a foamed surface as an implant as it is. Alternatively, the method of producing an implant further includes a step of immersing the article prepared by the latter method both in a first solution including calcium ions and a second solution including phosphate ions wherein the article may be first immersed in either of the first and second solutions. Both methods are capable of being carried out in a liquid phase, which makes it possible to easily produce implants even with a complicated shape.

BEST MODE TO CARRY OUT THE INVENTION

Figure 1:
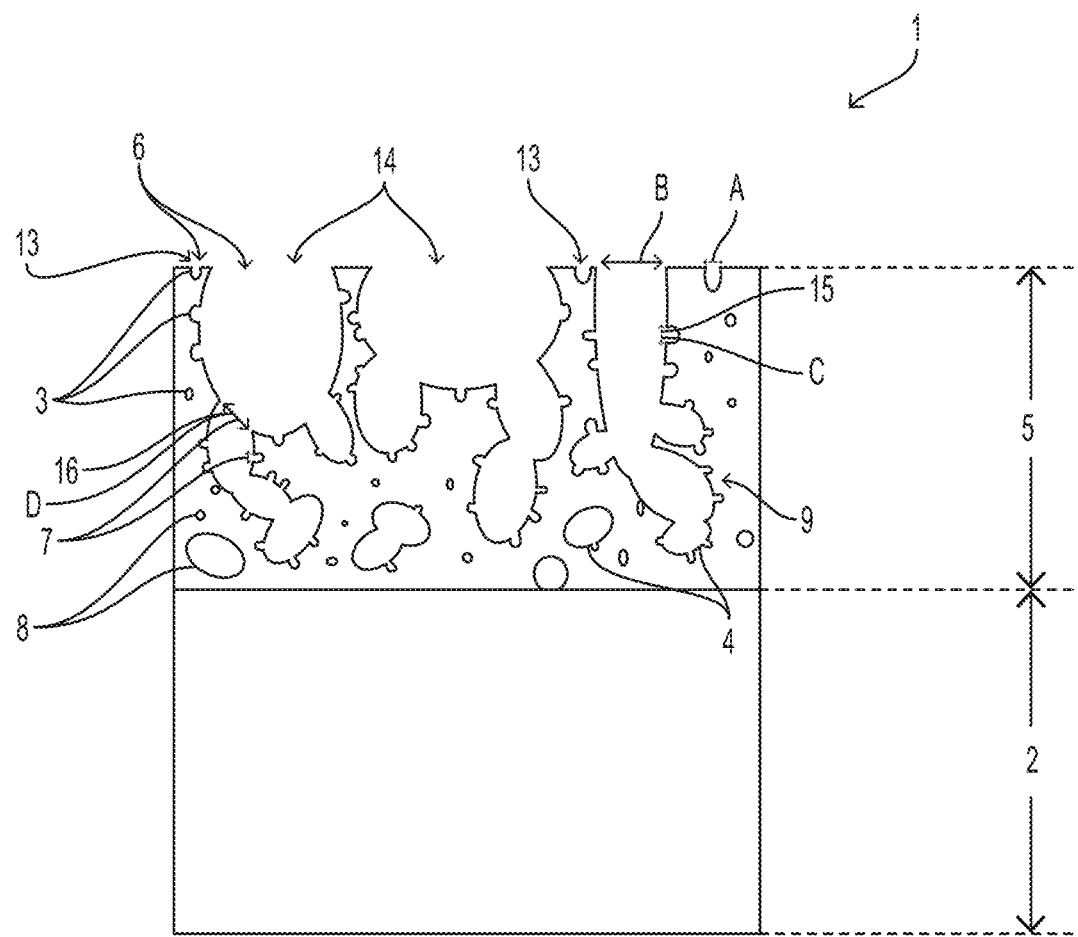
FIG. 1 shows a schematic illustration of an article with a foamed surface according to the present invention.

An example of the article with the foamed surface according to the present invention will be explained hereinafter, with FIG. 1 referred to. As shown in FIG. 1, an article with a foamed surface 1 of the present invention is one having a body 2 and a superficial layer 5, the surface of which includes many small pores with small diameters 3 and large pores with large diameters 4. The article 1 is made of a plastic. Part of the small pores 3 and the large pores 4 are open pores 6 which are in the surface of the superficial layer 5 and are open to the outside. The open pores 6 include small open pores 13 with an average diameter A of not more than 5 μm and large open pores 14 with an average diameter B from 10 to 200 μm. The large open pores 14, which are in the surface of the superficial layer and open to the outside, have an inner wall with passages 7 communicating with the small pores 3 and the large pores 4.

The superficial layer 5 includes a plurality of small pores 3 and large pores 4 with different pore sizes. These pores include isolated pores 8 that exist in isolation and connected pores 9 formed by two or more isolated pores connected with each other. Part of the small pores 3 and large pores 4 are open pores 6 which are in the surface of the superficial layer 5 and are open to the outside. The open pores 6 include small open pores 13 with an average diameter A of not more than 5 μm, preferably not more than 3 μm, and large open pores 14 with an average diameter B from 10 to 200 μm, preferably from 30 to 150 μm. The large open pores 14 have an inner wall with passages 7 connected and communicating with the small pores 3 and the large pores 4. One open pore 6 should preferably have more than one passage 7, or it should have one or more small-diameter passages 15 and one or more large-diameter passages 16. The small-diameter passage, which connects the open pore with a small pore 3, has a diameter C of not more than 5 μm, preferably not more than 3 μm. The large-diameter passage, which connects the open pore with a large pore 4, has a diameter D from 10 to 200 μm, preferably from 30 to 150 μm. The small and large pores are in the shape of a sphere, a flat sphere, an ellipsoid and/or a combination thereof. When an article with a foamed surface 1 according to the present invention is, for example, implanted in the body of a living organism as an implant, the superficial layer with such pores enables bone tissue, such as osteoblasts and osteoclasts, to penetrate into the inside of the superficial layer 5 through many open pores 6, which are in the surface of the superficial layer 5 and open to the outside, and passages 7, which connect the open pores 6 with small pores 3 and large pores 4 formed in the inside of the superficial layer. As a result, new natural bone is formed so that spaces existing in the inside of the superficial layer are filled. An implant capable of being integrated with native bone is thus provided. The more the large open pores 14 have passages 7, especially large-diameter passages 16, in the inner walls thereof, the deeper bone tissue is allowed to penetrate into the superficial layer 5 from the surface thereof and to let new born grow deep in the superficial layer 5, which leads to strong binding of the implant with the native bone.

The average diameter of the small open pores 13 and that of the large open pores 14 in the surface of the superficial layer 5 may be calculated based on images of the surface obtained through observation with a scanning electron microscope.

Firstly, a SEM image of the surface of a superficial layer 5 is obtained with a scanning electron microscope with a magnification set to, for example, 300 times. Then, a long diameter and a short diameter of relatively large open pores, for example those with the average diameter of about 10 μm or more, in the most superficial part of the layer, found within the entire visual field of the SEM image, are measured. Calculation of the arithmetic average of the measured values provides the average diameter of the large open pores 14.

Small open pores 13 normally exist in the framework between large open pores 14. When the diameters of the small open pores 13 are measured, the magnification of the scanning electron microscope should be further increased so that measurement errors will be reduced. For example, SEM images from a scanning electron microscope with a magnification set to 3000 times may be utilized. Then, a long diameter and a short diameter of the open pores in the framework are measured. In other words, a long diameter and a short diameter of all the open pores other than the large open pores 14 previously measured are measured. Calculation of the arithmetic average of the measured values provides the average diameter of the small open pores 13.

When the number of large open pores 14 or that of small open pores 13 on a SEM image is large, such as 50 or more, five straight lines should be randomly drawn across the SEM image first. Then, large open pores 14 or small open pores 13 on the lines are selected according to the criteria explained hereinbefore, and a long diameter and a short diameter thereof are measured. Calculation of the arithmetic average of the measured values provides the average diameter of the large open pores 14 or the small open pores 13.

The diameter of a passage 7, which is formed through connections of an open pore 6, open at the surface of the superficial layer 5, with small pores 3 and large pores 4, is measured from a SEM image with a predetermined magnification, in the same way as explained above. Another method may be a measurement with a mercury porosimeter.

There is no special limitation on the percentage of the area of the large open pores 14 in the most superficial part of the superficial layer 5 within a projected image of the most superficial part. When a surface foamed article of the present invention is utilized as an implant, however, the percentage should preferably be within a range of 10 to 95%, with a particularly preferable range of 20 to 85%. When the percentage of the area of the large open pores 14 are within the preferable range, the implant is capable of letting bone tissue into the inside of the superficial layer 5, which allows new bone to grow inside the superficial layer 5. As a result, an implant capable of binding with the native bone is provided.

The percentage of the area of the large open pores 14 in the most superficial part of the superficial layer 5 within a projected image of the most superficial part may be obtained in the following way: A photograph taken with a scanning electron microscope of the surface of a superficial layer 5 is made binary with an image processing software (e.g. "Scion Image" produced by Scion Corporation), into large open pores 14, or large pores 4 in the surface and open to the outside, and portions other than the large open pores. Calculation of the proportion of the area of the large open pores to that of the entire photograph provides the percentage.

There is no special limitation on the porosity of the small pores 3 and that of the large pores 4 in the superficial layer. However, the porosity of the small pores 3 should preferably be from 5 to 50%, particularly preferably from 10 to 40%, and the porosity of the large pores 4 should preferably be from 20 to 90%, particularly preferably from 30 to 80%, under the condition that the porosity of the sum of the small pores 3 and the large pores 4 be 99% or less. When the porosity of the small pores 3 is within the preferable range, the implant has many scaffolds to which substances involved in osteogenesis, such as proteins and cells, adhere, which facilitates the formation of new bone in the inside of the superficial layer. As a result, the article with the foamed surface 1 is strongly bound with the native bone. When the porosity of the large pores 4 is within the preferable range described above, bone tissue, after penetrating into the inside of the superficial layer 5, is easily kept in it, and spaces in which new bone is generated are ensured. New bone grows so as to fill the spaces with itself, which further strengthens the binding of the implant with the bone.

The porosity of the small pores 3 and that of the large pores 4 in the superficial layer 5 were obtained in the following way: A photograph taken with a scanning electron microscope of a section perpendicular to the surface of the superficial layer 5 is analyzed with an image processing software (e.g. "Scion Image" produced by Scion Corporation), so that the total area of the large pores 4 and that of the small pores 3 are respectively calculated. The porosities are obtained from this calculation. Images should be obtained by a scanning electron microscope with a magnification suitable to measure the area of the large pores 4 and that of the small pores 3, in the same way as in the calculation of the average diameters described hereinbefore. The proportion (a) of the area of the large pores to that of the entire image provides the porosity of the large pores (a×100(%)). The proportion (b) of the area of the small pores to that of the area of the entire image except the large pores provides the porosity of the small pores ((1-a)×b×100(%)).

The thickness of the superficial layer 5 is suitably decided depending on the part to which an article with a foamed surface 1 of the present invention is applied. For example, when an article with a foamed surface 1 of the present invention is used as an implant, the thickness should preferably be in a range of 10 to 1000 μm, particularly preferably in a range of 20 to 200 μm. The thickness within the preferable range allows bone tissue to penetrate into the inside of the superficial layer 5 from many open pores 6, which have openings in the surface of the superficial layer 5, through passages 7, which connect the open pores 6 with small pores 3 and large pores 4 formed in the inside of the superficial layer, once the implant is embedded in the body of a living organism. As a result, new bone generates and grows inside the superficial layer 5, which provides an implant capable of being bound with the native bone.

The material for the article with the foamed surface 1 of the present invention includes commonly used plastic. When the article 1 of the present invention is used as an implant, the material for the article 1 should preferably be a plastic whose mechanical properties are similar to those of bone or teeth. Specifically, the plastic should preferably have an elastic modulus from 1 to 50 GPa, and a flexural strength from 100 MPa or more.

The plastic whose mechanical properties are similar to those of bone or teeth includes engineering plastic or fiber-reinforced plastic. Examples of the engineering plastic may include polyamide, polyacetal, polycarbonate, polyphenylene ether, polyester, poly(phenylene oxide), poly(butylene terephthalate), poly(ethylene terephthalate), polysulfone, poly(ethersulfone), poly(phenylene sulfide), polyallylate, poly(ether imide), poly(etheretherketone), poly (amide imide), polyimide, fluororesin, ethylene-vinylalcohol copolymer, poly(methyl pentene), phenol resin, epoxy resin, silicone resin, diallyl phthalate resin, polyoxymethylene, and polytetrafluoroethylene.

Plastic for the matrix of the fiber-reinforced plastic may include, in addition to the engineering plastics listed above, for example, polyethylene, poly(vinyl chloride), polypropylene, EVA resin, EEA resin, 4-methylpentene-1 resin, ABS resin, AS resin, ACS resin, methyl methacrylate resin, ethylene-vinyl chloride copolymer, propylene-vinyl chloride copolymer, vinylidene chloride resin, poly(vinyl alcohol), poly(vinyl formal), poly(vinyl acetoacetal), poly(fluoroethylene-propylene), polytrifluorochloroethylene, methacrylate resin, polyaryletherketone, polyethersulfone, poly(ketone sulfide), polystyrene, polyaminobismaleimide, urea resin, melamine resin, xylene resin, isophthalic acid resin, aniline resin, furan resin, polyurethane, alkylbenzene resin, guanamine resin, and poly(diphenyl ether) resin.

When the article with the foamed surface 1 of the present invention is used as an implant, among those substances, poly(etheretherketone), which may sometimes be abbreviated to "PEEK" hereinafter, is particularly preferable for the material from which the article 1 is formed. PEEK has biocompatibility and mechanical properties close to those of bone. Therefore the employment of PEEK as material for the article with the foamed surface 1 provides, when the article is implanted as artificial bone in parts continuously bearing large load, a high-strength implant without stress shielding, or possible reduction in the amount of bone and decrease in the density thereof, caused by shielding of stress applied to bone.

The fiber for the fiber-reinforced plastic may include carbon fiber, glass fiber, ceramic fiber, metal fiber and organic fiber. The carbon fiber for this invention includes carbon nanotubes. Examples of the glass fiber may include fibers of borosilicate glass (E Glass), high strength glass (S Glass), and high-elasticity glass (YM-31A glass). The ceramic fiber may include fibers of silicon carbide, silicon nitride, alumina, potassium titanate, boron carbide, magnesium oxide, zinc oxide, aluminum borate, boron and the like. Examples of the metal fiber may include fibers of tungsten, molybdenum, stainless steel and tantalum. Examples of the organic fiber may include fibers of polyvinyl alcohol, polyamide, polyethylene terephthalate, polyester, aramid, and mixtures thereof.

The material for the surface foamed article 1 may include, if necessary, various additives such as an antistatic agent, an antioxidant, a light stabilizer such as hindered amine compounds, a lubricant, an anti-blocking agent, an ultraviolet absorber, an inorganic filler, and a colorant such as a pigment.

When the article with the foamed surface 1 of the present invention is used as an implant, the inner walls of the open pores 6 in the superficial layer 5 and/or the surface of the superficial layer 5 should preferably be provided with a bioactive substance. If a bioactive substance is carried on the inner walls and/or the surface, a chemical reaction takes place between the bioactive substance and bone tissue of the living organism once the implant is embedded in the body of a living organism, which expedites formation of new natural bone and results in a quick integration of the implant with the native bone.

Figures 2A, 2B:
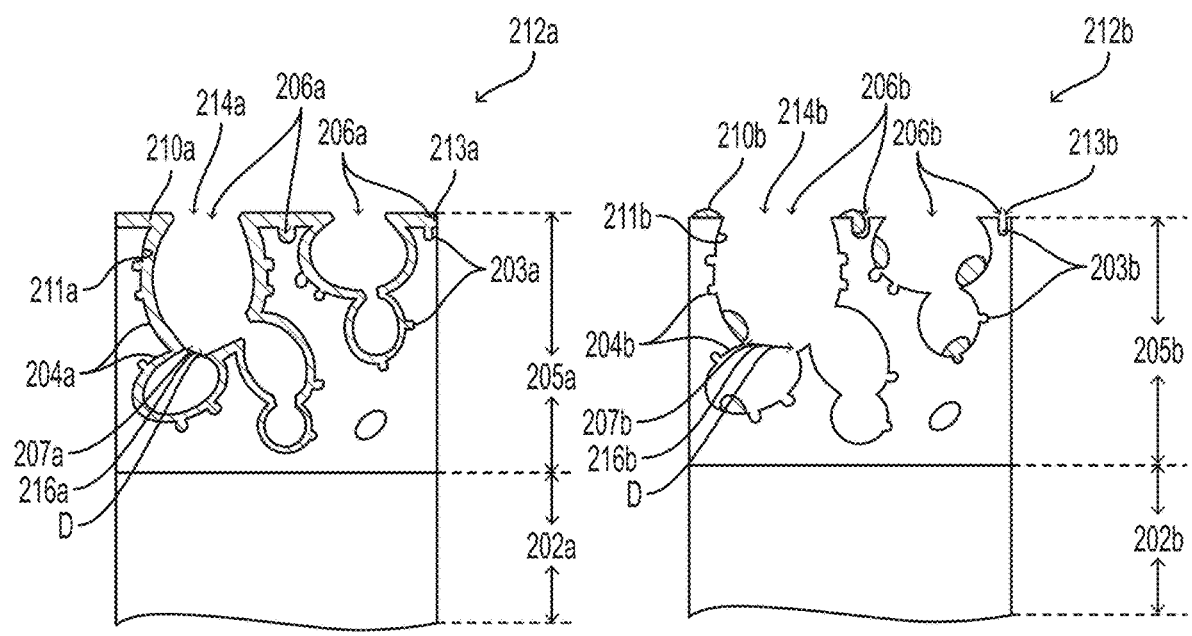
FIG. 2 Each of FIG. 2A and FIG. 2B (also referred herein as FIGS. 2(a) and 2(b), respectively) shows a schematic illustration of an implant having a bioactive substance.

FIGS. 2(a) and 2(b) show schematic illustrations of implants with a bioactive substance. As shown in FIG. 2(a), a bioactive substance 210a may be formed on the entirety of the inner walls 211a of the open pores 206a in the superficial layer 205a and on the entirety of the surface of the superficial layer 205a. As shown in FIG. 2(b), a bioactive substance 210b may be formed on parts of the inner walls of the open pores 206b and/or parts of the surface of the superficial layer 206b. When the inner walls 211a, 211b of the open pores 206a, 206b are provided with the bioactive substance 210a, 210b, the substance 210a, 210b should not be formed in such a way that all the open pores 206a, 206b are completely filled with the substance; as shown in FIGS. 2(a) and 2(b), part or all of the inner walls 211a, 211b of the open pores 206a, 206b should be covered with the bioactive substance 210a, 210b. For example, as shown in FIG. 2(a), a small open pore 213a may be completely filled with the bioactive substance 210a, whereas a large open pore 214a should preferably have the inner wall 214a thereof coated with the bioactive substance 210a, with the volume of the large open pore 214a kept essentially unchanged. In addition, a large-diameter passage 216a, which connects the large open pore with a large pore 204a, should not be stopped up with the bioactive substance 210a but should have a diameter D large enough to let bone tissue pass through the passage. An implant 212a having a superficial layer 205a with open pores 206a which communicate with the inner part of the layer through the large-diameter passage 216a, after the implant 212a is embedded in the body of a living organism, allows bone tissue to penetrate into the inside of the superficial layer 205a from the open pores 206a. As a result, a chemical reaction takes place between the bioactive substance 210a on the inner walls 211a of the open pores 206a and bone tissue of the living organism, which leads to the generation of new bone. The new bone grows so that the large open pore 214a, a small pore 203 communicating with the large open pore 214a, and the large pore 204a are filled with the new bone. Therefore new bone as well as the bioactive substance grows and spreads out in a complicated arborescent shape in the inside of the superficial layer 205a. In summary, when an implant has an open pore 206a, which is in the surface of the superficial layer 205a and is open to the outside, and a passage 207a, especially a large-diameter passage 216a, communicating with the open pore 206a, and a bioactive substance 210a on the inner wall 211a of the open pore 206a, the binding of the implant 212a with bone is expedited and strengthened.

When the respective images of the superficial layers 205a, 205b are projected, the proportion of the area of the wall and surface covered with the bioactive substance 210a, 210b should preferably be at least 5%, particularly preferably 20% or more within the projected images. In this context, the bioactive substance 210a, 210b includes not only the substance on the surface of the superficial layer 205a, 205b but also the substance on the inner wall 211a, 211b of the open pore 206a, 206b, capable of being recognized by the eye from the outside of the superficial layer 205a, 205b. When an implant includes the bioactive substance 210a, 210b on the inner wall 211a, 211b of the open pore 206a, 206b in the superficial layer 205a, 205b and/or on the surface of the superficial layer 205a, 205b, at a proportion within the preferable range mentioned above, a chemical reaction takes place between the bioactive substance 210a, 210b and bone tissue of a living organism once the implant is embedded in the body of the living organism, which expedites formation of new natural bone and results in a quick binding of the implant 212a, 212b with the native bone.

When the respective images of the superficial layers 205a, 205b are projected, the proportion of the area of the wall and surface covered with the bioactive substance 210a, 210b within the projected images may be obtained in the following way: An image taken with a scanning electron microscope of the surface of a superficial layer 205a or 205b is made binary with an image processing software (e.g. "Scion Image" produced by Scion Corporation), or into portions with the bioactive substance 210a, 210b and other portions. Calculation of the proportion of the area of the portions with the bioactive substance to that of the entire image provides the percentage.

The implant should include the bioactive substance 210a, 210b at a proportion from 0.5 to 30% to the volume of the superficial layer 205a, 205b. The bioactive substance 210a, 210b exists in separate spots on the inner walls 211a, 211b of the open pores 206a, 206b in the superficial layer 205a, 205b, and/or on the surface of the superficial layer 205a, 205b, and/or in the inside of the superficial layers 205, 205b; and/or these spots of the bioactive substance 210a, 210b are linked together so that the substance stretches into the inside of the superficial layers 205a, 205b in the shape of tree branches. Once the implant 212a, 212b with the bioactive substance 210a, 210b in the range of the amount described above in the superficial layer 205a, 205b is embedded in the body of a living organism, a chemical reaction takes place between the bioactive substance 210a, 210b and bone tissue of the living organism, which expedites formation of new natural bone and results in a quick integration of the implant 212a, 212b with the native bone.

The proportion of the volume of the bioactive substance 210a, 210b included in the superficial layer 205a, 205b may be obtained by a method similar to the method to obtain the proportion of the area of the bioactive substance 210a, 210b explained hereinbefore. Specifically, the proportion of the area of the bioactive substance 210a, 210b in a section perpendicular to the surface of the superficial layer 205a, 205b is calculated first. Then, the proportion of the volume of the bioactive substance 210a, 210b can be estimated based on the calculated values.

There is no special limitation on the bioactive substance 210a, 210b if it has high affinity with living organisms and it is capable of chemically reacting with bone tissue including teeth. Examples of such a substance may include calcium phosphate materials, bioglass, crystallized glass, which is also called "glass-ceramic", and calcium carbonate. Specific examples of the calcium phosphate materials may include calcium hydrogen phosphate, dibasic calcium phosphate hydrate, calcium dihydrogen phosphate, monobasic calcium phosphate hydrate, α-tricalcium phosphate, β-tricalcium phosphate, dolomite, tetracalciumphosphate, octacalciumphosphate, hydroxyapatite, fluoroapatite, carboxyapatite, and chlorapatite. Specific examples of the bioglass may include $SiO_2$—$CaO$—$Na_2O$—$P_2O_5$ glass, $SiO_2$—$CaO$—$Na_2O$—$P_2O_5$—$K_2O$—$MgO$ glass, and $SiO_2$—$CaO$—$Al_2O_3$—$P_2O_5$ glass. Specific examples of the crystallized glass may include $SiO_2$—$CaO$—$MgO$—$P_2O_5$ glass, which is also called "apatite-wollastonite crystallized glass", and $CaO$—$Al_2O_3$—$P_2O_5$ glass. These calcium phosphate materials, bioglass and crystallized glass are explained in detail in books such as "Chemical Handbook, the Volume of Adapted Chemistry" edited by the Chemical Society of Japan, published on Jan. 30, 2003 by MARUZEN Co., Ltd.; and "Clinical Application and Development of Bioceramics" written and edited by Hideki Aoki et al., published on Apr. 10, 1987 by Quintessence Publishing Co., Ltd.

Among these materials, the calcium phosphate materials are preferable for the bioactive substance 210a, 210b because of their excellence in bioactivity. Especially preferable is hydroxyapatite because it is excellent in stability in the body due to its resemblance to natural bone in structure and properties, and it does not show a remarkable solubility in the body.

Also, the bioactive substance 210a, 210b should preferably be low in crystallinity. The term "low in crystallinity" in this context means a state where the growth of the crystal is at a low degree. In the case of hydroxyapatite, the term means hydroxyapatites with scattering angles $2\theta=25.878°$ and the full width at half maximum of 0.2° or more in the spacing of lattice planes (d value) of 3.44 Å. Because the hydroxyapatite of bone is low in crystallinity wherein the full width at half maximum is about 0.4° under the above-mentioned conditions, a bioactive substance with a similar crystallinity, specifically with a full width at half maximum from 0.2 to 1° under the above-mentioned conditions, realizes a quick integration of the implant with the native bone.

When the bioactive substance is formed by a method which includes, for example, immersing the article with the foamed surface in a solution having calcium or phosphine, modifications to the kinds of components of the solution, the composition thereof, and/or the temperature at which the article is immersed in the solution will be able to adjust the crystallinity of the bioactive substance 210a, 210b.

An example of the method of producing an article with a foamed surface according to the present invention will be explained in the following.

Step 1 of the method includes preparation of a base with small pores, which has many small pores in the surface of the base made of a plastic material with a predetermined shape. For forming small pores in the surface of the plastic may be employed known methods. One of the known methods includes, for example, immersing a base made of a plastic in a corrosive solution, such as concentrated sulfuric acid, concentrated nitric acid or chromic acid, for a predetermined period of time; and then immersing the plastic base treated in the previous step in a washing solution that does not dissolve the plastic, such as pure water. When for example polyetheretherketone (PEEK) is employed for the plastic, the immersion of a PEEK base in concentrated sulfuric acid and subsequently in pure water is capable of forming small pores in the base.

The pores formed in the surface of the plastic base should have such a diameter as to enable a foaming agent to be used in step 2 to penetrate into the inside of the plastic base. The diameter may be suitably chosen depending on the kind of foaming agent. When for example sodium carbonate is employed for the foaming agent, the diameter of the small pores should preferably be from 0.1 to 200 µm. The surface of the plastic base should include small pores at such a porosity that they are capable of sufficiently holding the foaming agent to be used in step 2. When the foaming agent is, for example, sodium carbonate, the layer of the plastic base in which small pores are formed should preferably have a porosity of the range of 10 to 90%. When the porosity has a smaller value within the range, each pore should be formed so that a foaming agent will be held at a desired depth from the surface of the plastic base; a plurality of connected pores may be formed from the surface of the plastic base toward the inside thereof; or columnar pores perpendicular to the surface of the base may extend from the surface of the plastic base to the inside thereof. The layer with many pores formed therein should have a thickness roughly the same as that of the article with the foamed surface, the final product. Specifically, the thickness should be preferably from 10 to 1000 µm. When the corrosive solution for PEEK is for example concentrated sulfuric acid, modifications to a time period for and/or a temperature at which the PEEK base is immersed in concentrate sulfuric acid may be used to control the thickness of the layer with many pores. Also, modifications to the kind of the washing solution and/or the temperature at which the article is immersed in the washing solution after the immersion in the concentrated sulfuric acid will be able to adjust the diameter of the pores and the porosity.

Step 2 includes immersing the base with small pores prepared in step 1 in a solution including a foaming agent for a predetermined period of time, thereby preparing a foaming agent-holding base, which holds the foaming agent at the surface of the base with many small pores. The foaming agent may be anything as long as it is a substance capable of forming a desired porous structure at the surface of the plastic base. Examples of the foaming agent may include inorganic foaming agents such as carbonate salts and aluminum powder, and organic foaming agents such as azo compounds and isocyanates. When the article with the foamed surface, which is the final product, is applied to an implant, the foaming agent should be a substance that is harmless to living organisms. Carbonates are preferably used as the harmless foaming agent. Examples of the carbonates may include sodium bicarbonate, sodium carbonate and potassium carbonate.

Step 3 includes immersing the foaming agent-holding base obtained in step 2 for a predetermined period of time in a foaming solution capable of making the plastic swell and the foaming agent foam, thereby allowing the swelling and the foaming to progress simultaneously to the preparation of a foamed base. The foaming solution may include an acid solution, such as concentrated sulfuric acid, hydrochloric acid and nitric acid. When the foaming agent-holding base is made of PEEK and the foaming agent is a carbonate, the foaming solution should preferably be concentrated sulfuric acid with a concentration of 90% or more.

Step 4 prepares an article with a foamed surface, which includes immersing the foamed base obtained in step 3 in a coagulating solution that coagulates the swollen plastic. The coagulating solution, which must not dissolve the plastic, may include an aqueous solution such as water, acetone and ethanol. When the foamed base is made of PEEK, the coagulating solution may further include an aqueous solution of an inorganic acid such as an aqueous sulfuric acid solution with a concentration of less than 90%, an aqueous nitric acid solution, an aqueous phosphoric acid solution and an aqueous hydrochloric acid solution, and a water-soluble organic solvent. Examples of the water-soluble organic solvent may include N-methyl-2-pyrrolidone; dimethyl formamide; dimethyl acetoamide; dimethyl sulfoxide; tetrahydrofuran; alcohols such as ethylene glycol, diethylene glycol, triethylene glycol, propylene glycol, dipropylene glycol, glycerin ethanol, propanol, butanol, pentanol and hexanoyl, and aqueous solutions thereof; and liquid polymers such as polyethylene glycol, polypropylene glycol and polyvinyl pyrrolidone, or aqueous solutions thereof and mixtures thereof.

The foamed base obtained in step 3 may be immersed in at least one solution selected from the kinds of solutions capable of being used for the coagulating solution, or several kinds of such solutions one by one. Also, a mixture of at least two such solutions may be used for the coagulating solution.

Preferably substances remaining on the article with the foamed surface, such as the foaming agent and the coagulating solution, should be washed off with pure water after step 4.

The porous structure formed in the surface of the plastic base, i.e. the diameter of the large open pores, that of the small open pores, that of the passages, and the porosity, which define the porous structure of the superficial layer of the surface foamed article, may be controlled through suitable selection of factors such as the kind and concentration of the foaming agent, the kind and concentration of the foaming solution, the time period for which the foaming agent-holding base is immersed in the foaming solution, the kind and concentration of the coagulating solution, the time period for which the foamed base is immersed in the coagulating solution, and the temperature in each step.

If at least one parameter selected especially from the kind of the coagulating solution, the concentration thereof and the time period for which the foamed base is immersed therein, among these parameters, is changed, it will lead to an easy production of an article with a foamed surface whose superficial layer has a desired porous structure. Changes in these parameters are capable of controlling the coagulating rate of the swollen plastic in the surface of the foamed base. For the coagulating solution, preferable are water, and at least one slow coagulating solution which takes a longer time to coagulate the swollen plastic than water. When the material of the foamed base is PEEK, the slow coagulating solution may be an aqueous sulfuric acid solution with a concentration of less than 90%.

When a foamed base made of, for example, PEEK is immersed in, as coagulating solution, an aqueous sulfuric acid solution with a concentration of 86%, PEEK coagulates moderately compared with the case where the foamed base is immersed in water. In other words, the coagulating speed is slowed down. This slowness allows the porous structure in the surface of the foamed base to change with time while the foamed base is being immersed in the coagulating solution.

Changes in the structure of the surface of the foamed base caused by a difference in the time period for which the foamed base is immersed in a slow coagulating solution will be explained hereinafter, with a large-diameter passage 16 formed by the connection of two large pores 4, and with a small pore 3.

The diameter of the large open pores 14, or the large pores 4 which are at the surface and open to the outside, and the diameter of the large-diameter passages 16 become larger gradually in course of the period of time for which the foamed base is immersed in the coagulating solution. After a predetermined period of time, they turn to becoming smaller. The number of large open pores 14 and large-diameter passages 16 decreases in course of the period of time for which the foamed base is immersed in the coagulating solution. It is supposed that the reason why the diameters become larger with time is that a plurality of pores generated by the foaming agent become connected and larger while the swollen PEEK is coagulating moderately. On the other hand, we think the reason why the diameters turn to becoming smaller after a predetermined period of time in the following way: The effect of the foaming agent is weakened while the swollen PEEK is coagulating moderately, which makes smaller the diameter of all the pores including enlarged pores due to the connection. Also, it is surmised that the reason for the decrease in the number of large open pores 14 and large-diameter passages 16 in course of the period of time for which the foamed base is immersed in the coagulating solution is that large open pores 14 and large-diameter passages 16 are linked and unified while the swollen PEEK is coagulating moderately.

The diameter of the small open pores 13, or the small pores 3 which are at the surface and open to the outside, and the porosity become smaller gradually in course of the period of time for which the foamed base is immersed in the coagulating solution. Large pores are formed by the action of the foaming agent, whereas it is considered that small pores are formed by phase separation of the swollen PEEK. The phase separation does not tend to occur between the swollen PEEK and a slow coagulating solution that coagulates the PEEK moderately. It is thought that the longer the period of time for which the foamed base is immersed in a slow coagulating solution is made, the smaller the number of small open pores 13 and the diameter thereof as well as the porosity are made.

As explained hereinbefore, the difference in the period of time for which the foamed base is immersed in a slow coagulating solution may lead to the production of articles 1 with a foamed surface whose superficial layers 5 have different porous structures. In particular, if a foamed base is transferred to a coagulating solution capable of coagulating swollen plastic quickly, such as water, at the point of time when the diameter of the large open pores 14 and that of the large-diameter passages become the largest, the coagulation is immediately completed, which provides a surface foamed article 1 with good connection of pores toward the inside of the superficial layer 5.

The explanation that has been made so far takes an 86% aqueous solution of sulfuric acid as an example of the coagulating solution. When an aqueous solution of sulfuric acid with a less concentration is used as a slow coagulating solution, the manner of changing in the structure at the surface of a foamed base is different. When an aqueous sulfuric acid solution with a less concentration is used, the swollen PEEK coagulates in a shorter period of time than it does when an 86% aqueous sulfuric acid solution is used, which may lead to the coagulation of the large pores 4 before the effect of the foaming agent is weakened. In this case, a longtime immersion of the foamed base in the coagulating solution will neither make smaller the diameter of the large pores 14 and that of the large passages 16 nor the number thereof.

As explained hereinbefore, how the structure at the surface of the foamed base changes in course of the period of time for which the foamed base is immersed in the coagulating solution is different depending on the kind and concentration of the slow coagulating solution. Therefore, if one chooses a desired slow coagulating solution, immerses a foamed base in it for a predetermined period of time, and transfers the base into water at the point of time when the surface of the foamed base has a desired porous structure, which immediately completes the coagulation of the swollen plastic, an article with a foamed surface whose superficial layer 5 has a desired porous structure is obtained. As a method of coagulating the swollen plastic other than the immersion of it in water, the swollen plastic may be kept in a slow coagulating solution for a time period sufficient to coagulate completely.

In the following will be explained an example of the method for producing an implant with a bioactive substance on the surface of the superficial layer and/or in the inside thereof wherein an article with a foamed surface prepared by the method explained hereinbefore is applied to the implant.

The bioactive substance may be formed by any method as long as it is fixed to the inner walls of open pores in the superficial layer and/or on the surface of the superficial layer. An example of the method may be a liquid phase method in which an article with a foamed surface prepared through steps 1-4 is immersed both in a first solution including at least 10 mM of calcium ions and a second solution including at least 10 mM of phosphate ions wherein the article with the foamed surface may be first immersed in either of the first and second solutions.

An example of the method of producing an implant with the liquid phase method will be explained hereinafter.

Firstly, an article with a foamed surface prepared through steps 1-4 is immersed in a first solution including at least 10 mM of calcium ions for a predetermined period of time. There is no special limitation on the first solution as long as it includes at least calcium ions. The first solution may further include other ions such as sodium ions, potassium ions, magnesium ions, carbonate ions, silicate ions, sulfate ions, nitrate ions, chloride ions and hydrogen ions, while preferably the first solution should substantially not include phosphate ions. The first solution including calcium ions may usually be aqueous solutions of chemical compounds which have high water-solubility and do not exert a bad influence on the human body. Examples of the first solution may include aqueous solutions of calcium chloride, calcium hydroxide, calcium nitrate, calcium formate, calcium acetate, calcium propionate, calcium butyrate, calcium lactate, and mixed solutions thereof. Among them preferable is an aqueous solution of calcium chloride.

After the immersion in the first solution including calcium ions for a predetermined period of time, the article is immersed in a second solution including at least 10 mM of phosphate ions. There is no special limitation on the second solution as long as it includes at least phosphate ions. The second solution may further include other ions such as sodium ions, potassium ions, magnesium ions, carbonate ions, silicate ions, sulfate ions, nitrate ions, chloride ions and hydrogen ions, while preferably the second solution should substantially not include calcium ions. The second solution including phosphate ions may usually be aqueous solutions of chemical compounds which have high water-solubility and do not exert a bad influence on the human body. Examples of the second solution may include aqueous solutions of phosphoric acid, disodium hydrogen phosphate, sodium dihydrogen phosphate, dipotassium hydrogen phosphate, potassium dihydrogen phosphate, and mixed solutions thereof. Among them preferable is an aqueous solution of dipotassium hydrogen phosphate.

There is no special limitation on the order of immersion in the two solutions. However, when hydroxyapatite as bioactive substance is prepared in the inside of the superficial layer, i.e. in the porous structure, the preparation reaction should proceed in an alkaline medium where hydroxyapatite shows less solubility, from the viewpoint of the production amount. Therefore the solution in which the article with the foamed surface is immersed later should be alkaline, specifically with a pH from 8 to 10.

The time period for which the article is immersed in each of the first solution including at least calcium ions in an amount of at least 10 mM and the second solution including at least phosphate ions in an amount of at least 10 mM should be preferably from 1 minute to 5 hours, particularly preferably from 3 minutes to 3 hours. The immersion within the range of 1 minute to 5 hours enables calcium ions and phosphate ions to sufficiently permeate into the inside of the article with the foamed surface, and allows a bioactive substance to be produced on and fixed to the inner walls of the open pores and passages in the superficial layer of the article. If an increase in the amount of the produced bioactive substance is desired, the operation of immersing the article in each solution may be carried out several times.

In the final step, the article with the foamed surface carrying the bioactive substance produced therein is washed in pure water and dried. Thus obtained is an implant having an article with a foamed surface carrying a bioactive substance on the inner walls of at least open pores in the superficial layer thereof and/or the surface of the superficial layer thereof.

The method of producing a bioactive substance is not limited to that explained above. Another method may include steps of immersing an article with a foamed surface in a solution that contains a great amount of a bioactive substance; drying the resulting article, thereby fixing the bioactive substance onto the inside of the superficial layer having the porous structure in the article; washing the resultant in pure water; and drying the obtained again.

The method according to the present invention may be used to produce articles with a foamed surface other than the article 1 of the present invention. The produced articles have various uses including implants. When applied to implants, they are used in various shapes, such as granules, fibers, blocks or films, depending on the parts in the body of a living organism. Preferably the implant should be formed, corrected and/or made into a shape which is essentially the same as the shape of the defective part of bone or a tooth that is about to be filled with this implant, or a shape which corresponds to the shape thereof, such as a similar shape.

Either a method of forming, correcting and/or making a blank made of a plastic such as PEEK into a plastic base with a desired shape which is followed by forming a superficial layer with a porous structure in the surface of the plastic base, or a method of forming a superficial layer with a porous structure in the surface of a plastic blank which is followed by correcting and/or making the plastic blank into a plastic base with a desired shape provides an article with a foamed surface according to the invention. The employment of the liquid phase method described hereinbefore to prepare an article with a foamed surface facilitates a formation of the superficial layer with a porous structure in the surface part of the plastic base after a blank made of a plastic such as PEEK is formed, corrected and/or made into a plastic base with a complicated shape.

The superficial layer may be formed in the entire surface of a plastic base. Alternatively, when the article with the foamed surface is used as an implant, the superficial layer may be formed only in the parts of the surface that require bonding with bone or teeth. The article with the foamed surface may also be applied to an implant with a bioactive substance at least on the inner walls of open pores in the superficial layer and/or on the surface of the superficial layer.

The article with the foamed surface and the implant with a bioactive substance may be applied to bone fillers, artificial joints, bone connecting materials, artificial vertebral bodies, spacers between vertebral bodies, cages between vertebral bodies and dental implants.

EXAMPLES

The invention is described by way of working examples, which impose no limitations on the present invention.

Preparation and Evaluation of Article with Foamed Surface

Working Example 1

This is a working example in which PEEK was used as material for an article with a foamed surface.

The article was prepared through the following steps.

A surface of a disc (with 10 mm in diameter and 2 mm in thickness, a 450G product manufactured by Victrex Corporation) was ground with #1000 sandpaper. The ground disc was immersed in concentrated sulfuric acid whose concentration was 97% for five minutes. The disc was taken out of the sulfuric acid and then immersed in pure water for five minutes. Subsequently, the disc was repeatedly washed until the pH of pure water used for the washing turned neutral. A micro-porous base with micro pores in the surface thereof was obtained. An observation of the surface of the micro-porous base with a scanning electron microscope revealed that the surface had many pores with a diameter from 1 to 2 µm and the inside of the surface had a network structure.

Then the obtained micro-porous base was immersed in an aqueous solution of sodium bicarbonate with a concentration of 500 mM for 60 minutes, which allowed the micro-porous base to hold sodium bicarbonate at the surface thereof. A foaming agent-holding base was thus prepared.

The foaming agent-holding base was immersed for one minute in concentrated sulfuric acid whose concentration was 97% and which was a foaming solution, which allowed the surface of the PEEK of the foaming agent-holding base to swell and simultaneously the sodium bicarbonate held by the base to foam. A foamed base was thus prepared.

The foamed base was taken out of the concentrated sulfuric acid. It was then immersed in pure water for ten minutes, which coagulated the surface of the PEEK. The resultant was washed repeatedly until the pH of pure water used for the washing turned neutral. The washed base was dried at 120° C. for three hours, which provided an article with a foamed surface.

Figure 3:
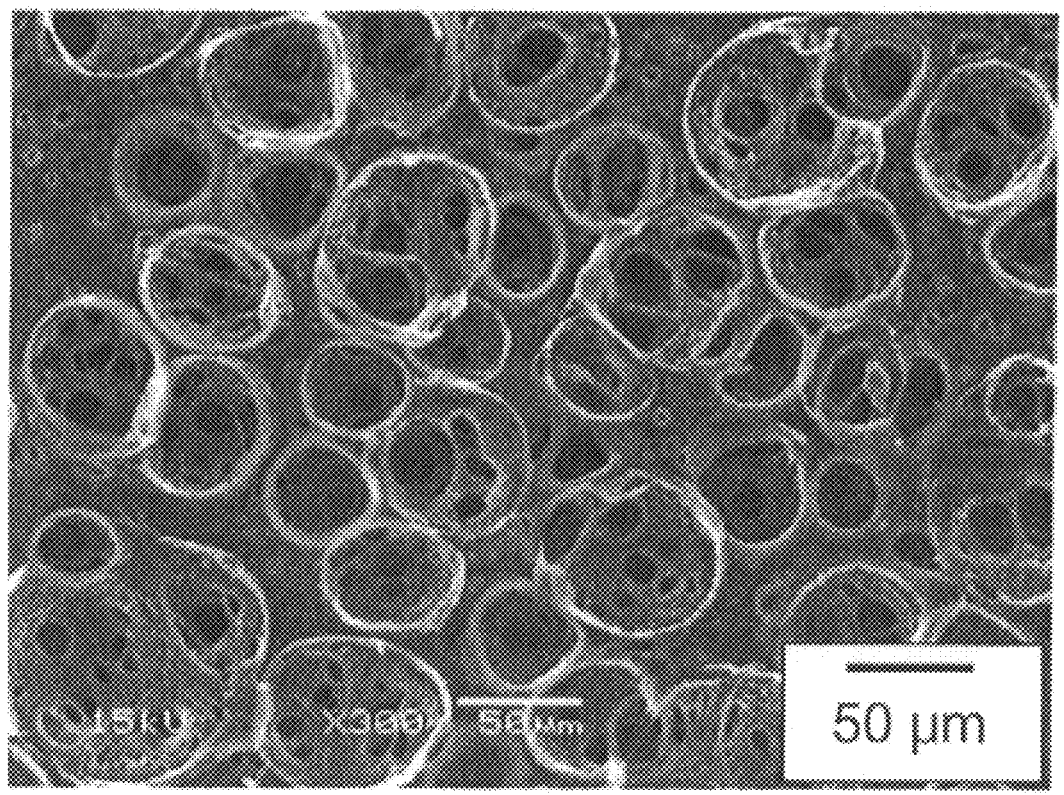
FIG. 3 is a photograph of the surface of the article with the foamed surface prepared in Working Example 1, obtained with a scanning electron microscope.

The surface of the prepared article was observed under a scanning electron microscope at 300 magnifications. The resulting image is shown in FIG. 3. Many small open pores originating from small pores with a diameter from 1 to 5 µm and many large open pores originating from large pores with a diameter from 50 to 100 µm were observed. Also observed were many small-diameter passages connecting large open pores with small pores and many large-diameter passages connecting large open pores with large pores in the inner walls of the large open pores.

A long diameter and a short diameter of each of the large open pores and small open pores were measured by the method explained hereinbefore based on a photograph taken with a magnification of 3000 times and a photograph with a magnification of 300 times. Calculation of the arithmetic average of the measured values provided the average diameter of the small open pores and that of the large open pores: The former was 2 µm, and the latter was 73 µm.

A photograph taken with a scanning electron microscope of the surface of the surface foamed article was made binary with an image processing software (specifically "Scion Image" produced by Scion Corporation), into large open pores and portions other than the large open pores. The proportion of the area of the large open pores to that of the entire photograph was calculated, and it was 78%.

Figure 4:
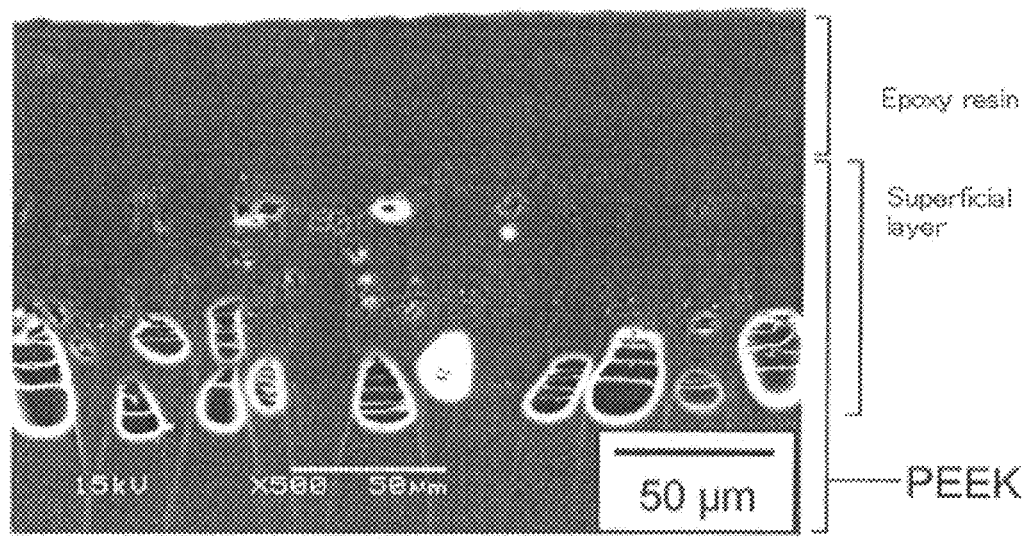
FIG. 4 is a photograph of a section of the article with the foamed surface prepared in Working Example 1, obtained with a scanning electron microscope.

A section perpendicular to the surface of the prepared article was observed under a scanning electron microscope at 500 magnifications. The resulting image is shown in FIG. 4. A layer with a thickness of approximately 70 µm that included many pores was observed in the surface of the article.

Photographs of a section perpendicular to the surface of a test piece, which was the superficial layer of the prepared article, were taken with a scanning electron microscope with a magnification of 3000 times and a magnification of 300 times. The photographs were processed with an image processing software ("Scion Image" produced by Scion Corporation), and the total area of the small pores and that of the large pores are respectively calculated. The porosity of the small pores and that of the large pores were calculated respectively from the proportion of the area of the small pores to that of the entire photograph and the proportion of the area of the large pores to that of the entire photograph, as explained hereinbefore. As a result, the porosities of the small pores and the large pores were respectively 18% and 64%.

The diameters of the passages in the superficial layer, having many pores, of the prepared article were measured with a mercury porosimeter. It was observed that the amount of mercury injected into the superficial layer was larger than that of mercury injected into unprocessed control PEEK, in the diameter range of 1 to 100 µm. This observation meant that passages having a diameter in this range were formed with a wide distribution of diameters. This result was consistent with the result of an observation of the superficial layer with a scanning electron microscope.

Working Example 2

An article with a foamed surface was obtained with the same method as in Working Example 1, except that an aqueous solution of sodium carbonate whose concentration was 500 mM was used in place of the aqueous solution of sodium bicarbonate.

Figure 5:
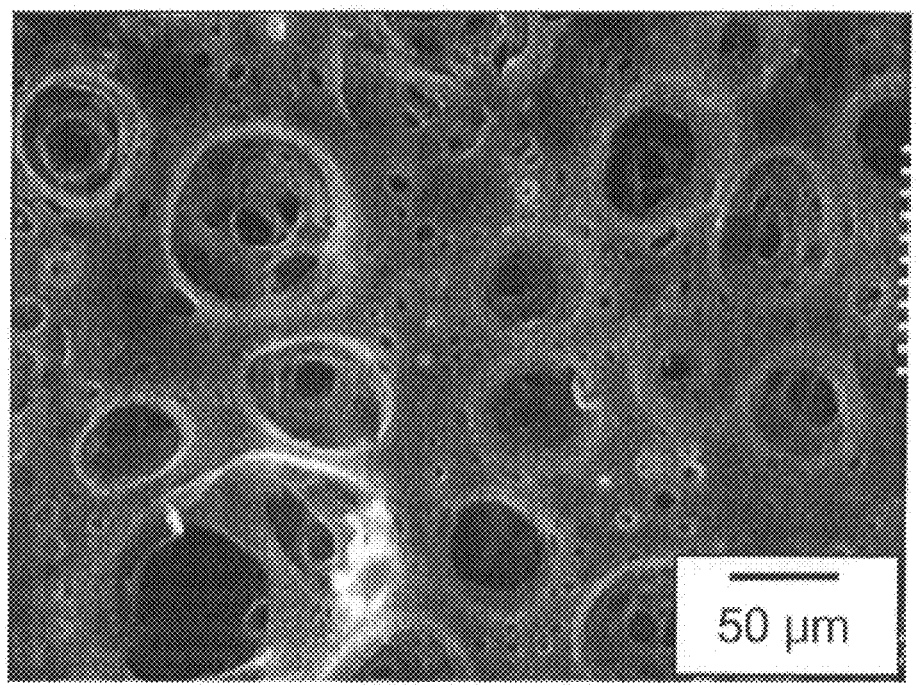
FIG. 5 is a photograph of the surface of the article with the foamed surface prepared in Working Example 2, obtained with a scanning electron microscope.

The surface of the prepared article was observed under a scanning electron microscope at 300 magnifications. The resulting image is shown in FIG. 5. Many open pores and many passages formed in the inner walls of the open pores were observed in the surface of the article, in the same way as in Working Example 1. Small open pores originating from small pores had a diameter ranging from 2 to 4 µm, and large open pores originating from large pores had a diameter ranging from 30 to 80 µm.

The average diameter of the small open pores and that of the large open pores were calculated with the same method as in Working Example 1: The former was 3.1 µm, and the latter was 45 µm.

The proportion of the area of the large open pores to that of the entire photograph was calculated with the same method as in Working Example 1, and it was 39%.

Working Example 3

An article with a foamed surface was obtained with the same method as in Working Example 1, except that an aqueous solution of potassium carbonate whose concentration was 500 mM was used in place of the aqueous solution of sodium bicarbonate.

Figure 6:
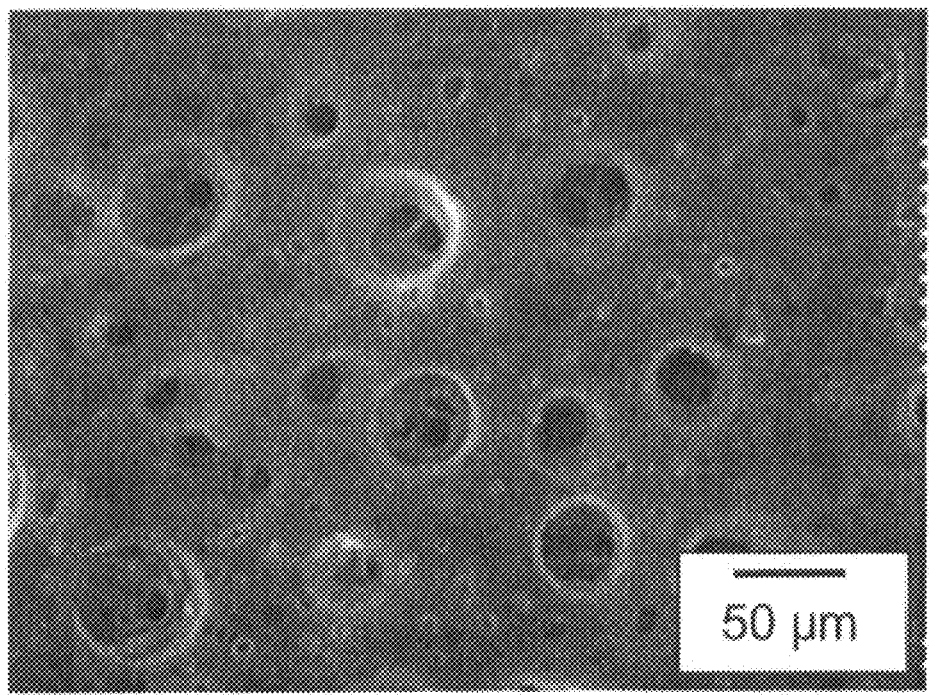
FIG. 6 is a photograph of the surface of the article with the foamed surface prepared in Working Example 3, obtained with a scanning electron microscope.

The surface of the prepared article was observed under a scanning electron microscope at 300 magnifications. The resulting image is shown in FIG. 6. Many open pores and many passages formed in the inner walls of the open pores were observed in the surface of the article, in the same way as in Working Example 1. Small open pores originating from small pores had a diameter ranging from 1 to 2 µm, and large open pores originating from large pores had a diameter ranging from 20 to 30 µm.

The average diameter of the small open pores and that of the large open pores were calculated with the same method as in Working Example 1: The former was 1.6 µm, and the latter was 23 µm.

The proportion of the area of the large open pores to that of the entire photograph was calculated with the same method as in Working Example 1, and it was 15%.

Working Example 4

An article with a foamed surface was obtained with the same method as in Working Example 3, except that the concentration of the aqueous solution of potassium carbonate was changed to 3 M.

Figure 7:
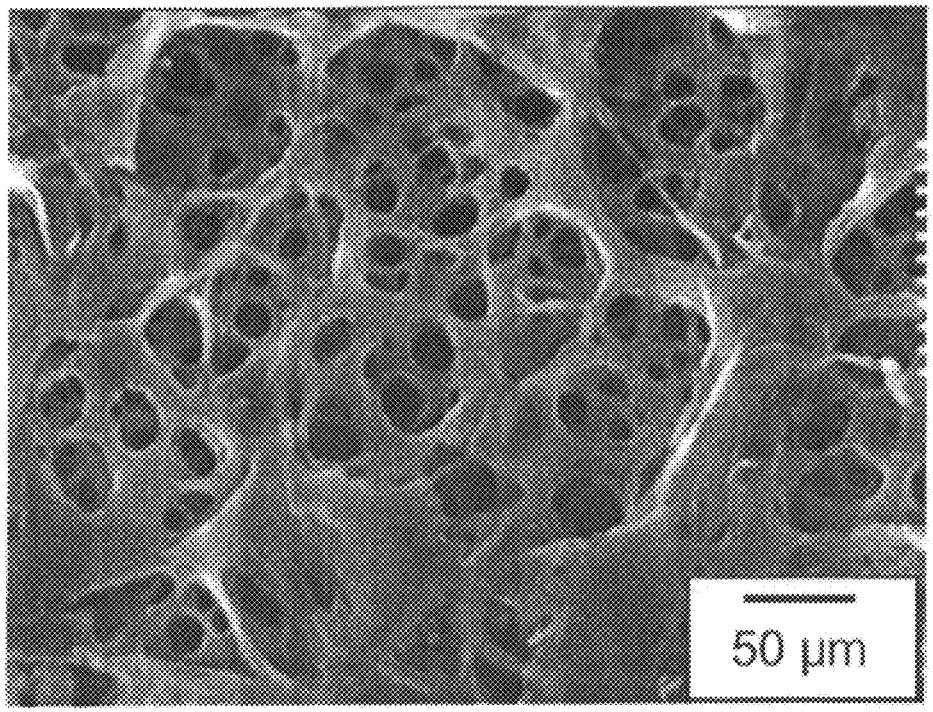
FIG. 7 is a photograph of the surface of the article with the foamed surface prepared in Working Example 4, obtained with a scanning electron microscope.

The surface of the prepared article was observed under a scanning electron microscope at 300 magnifications. The resulting image is shown in FIG. 7. Many open pores and many passages formed in the inner walls of the open pores were observed in the surface of the article, in the same way as in Working Example 3. Small open pores originating from small pores had a diameter ranging from 1 to 4 µm, and large open pores originating from large pores had a diameter ranging from 100 to 200 µm.

The average diameter of the small open pores and that of the large open pores were calculated with the same method as in Working Example 1: The former was 2.4 µm, and the latter was 106 µm.

The proportion of the area of the large open pores to that of the entire photograph was calculated with the same method as in Working Example 1, and it was 64%.

Working Example 5

An article with a foamed surface was obtained with the same method as in Working Example 4, except that the foamed base was immersed in an aqueous solution of sulfuric acid with a concentration of 63% for one minute, after the foamed base was taken out of the concentrated sulfuric acid and before it was immersed in pure water for ten minutes.

Figure 8A:
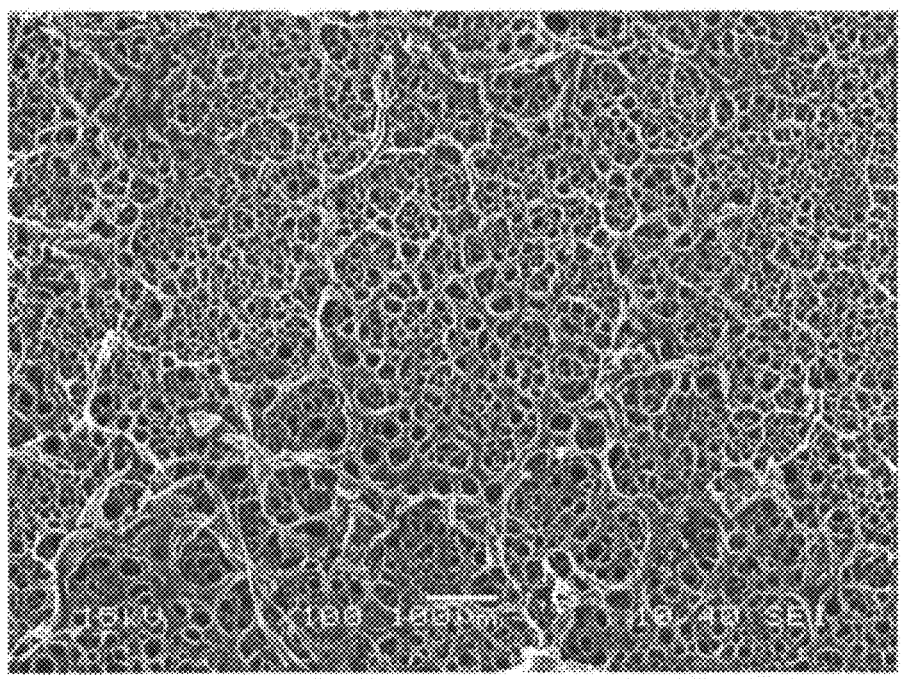
FIGS. 8A and 8B (also referred herein as FIGS. 8(a) and 8(b), respectively) are photographs of the surface of the article with the foamed surface prepared in Working Example 5, obtained with a scanning electron microscope.

The surface of the prepared article was observed with a scanning electron microscope. An image obtained at 100 magnifications is shown in FIG. 8(a), and an image at 3000 magnifications in FIG. 8(b). As shown in FIG. 8(a), many open pores and many passages formed in the inner walls of the open pores were observed in the surface of the article, in the same way as in Working Example 4. The number of passages was essentially the same as that of passages in the article obtained in Working Example 4. Large open pores originating from large pores had a diameter ranging from 10 to 100 µm.

Figure 8B:
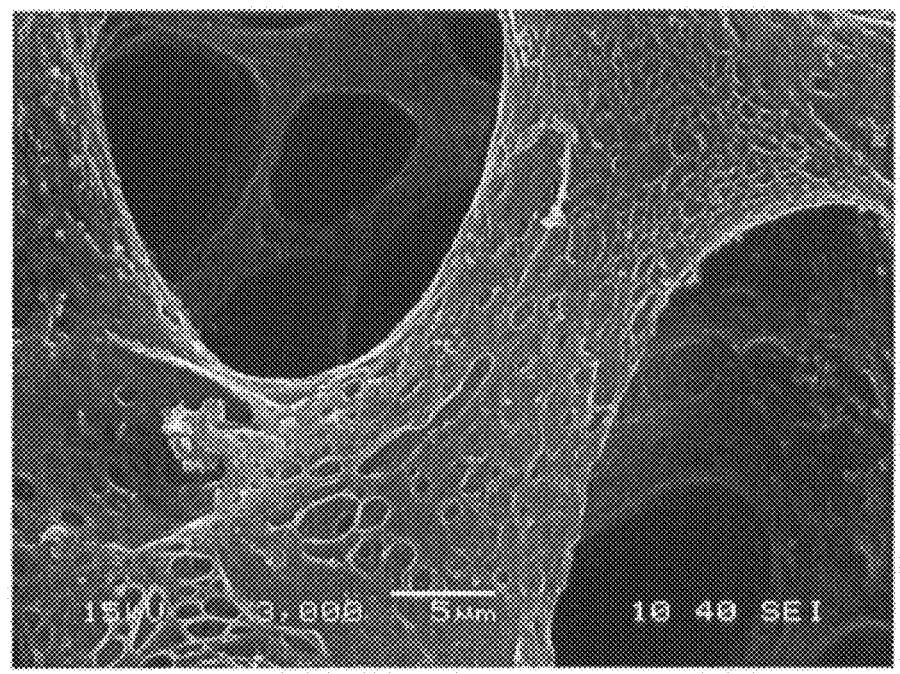

As shown in FIG. 8(b), small open pores originating from small pores had a diameter ranging from 0.2 to 4 µm.

The average diameter of the small open pores and that of the large open pores were calculated with the same method as in Working Example 1: The former was 1.4 µm, and the latter was 39 µm.

The proportion of the area of the large open pores to that of the entire photograph was calculated with the same method as in Working Example 1, and it was 61%.

Working Example 6

An article with a foamed surface was obtained with the same method as in Working Example 5, except that the period of time for which the foamed base was immersed in the 63% aqueous solution of sulfuric acid was changed to five minutes.

Figure 9A:
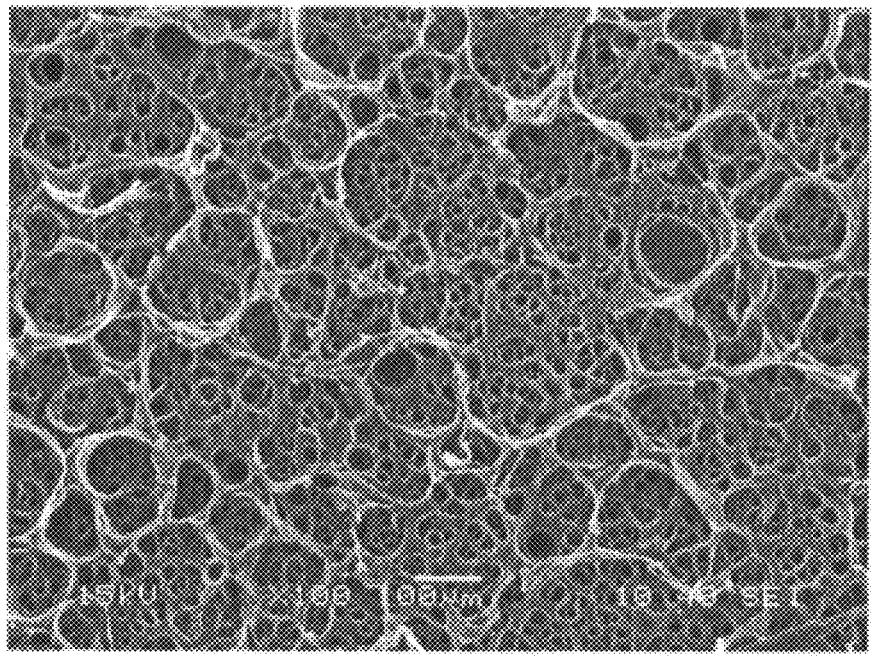
FIGS. 9A and 9B (also referred herein as FIGS. 9(a) and 9(b), respectively) are photographs of the surface of the article with the foamed surface prepared in Working Example 6, obtained with a scanning electron microscope.

The surface of the prepared article was observed with a scanning electron microscope. An image obtained at 100 magnifications is shown in FIG. 9(a), and an image at 3000 magnifications in FIG. 9(b). As shown in FIG. 9(a), many open pores and many passages formed in the inner walls of the open pores were observed in the surface of the article, in the same way as in Working Example 5. The number of passages was a little smaller than that of passages in the article obtained in Working Example 5. Large open pores originating from large pores had a diameter ranging from 30 to 300 µm, which was larger than the diameter of the large open pores included in the article of Working Example 5.

Figure 9B:
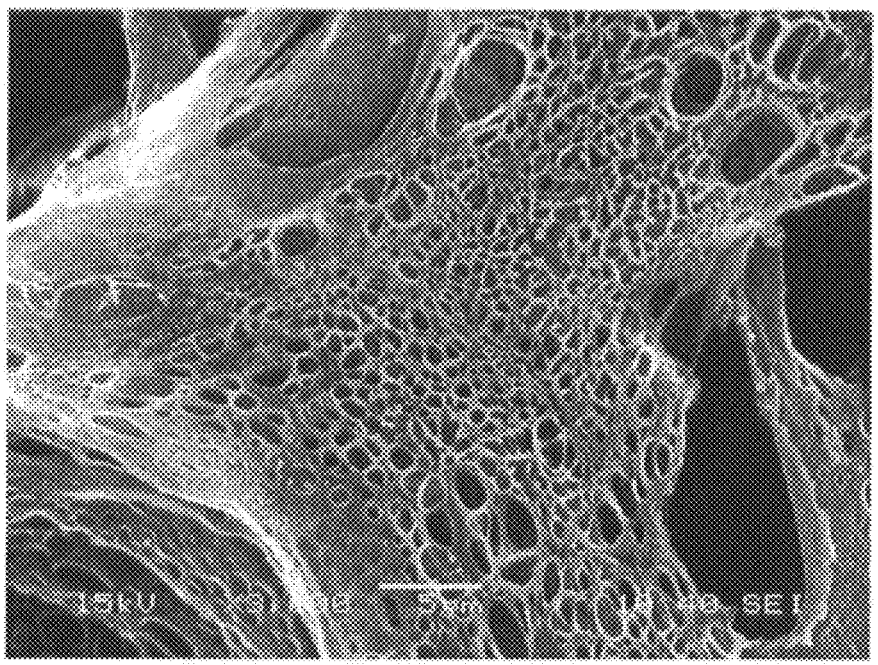

As shown in FIG. 9(b), small open pores originating from small pores had a diameter ranging from 0.5 to 5 µm.

The average diameter of the small open pores and that of the large open pores were calculated with the same method as in Working Example 1: The former was 1.4 µm, and the latter was 118 µm.

The proportion of the area of the large open pores to that of the entire photograph was calculated with the same method as in Working Example 1, and it was 67%.

Working Example 7

An article with a foamed surface was obtained with the same method as in Working Example 5, except that the period of time for which the foamed base was immersed in the 63% aqueous solution of sulfuric acid was changed to 15 minutes.

Figure 10A:
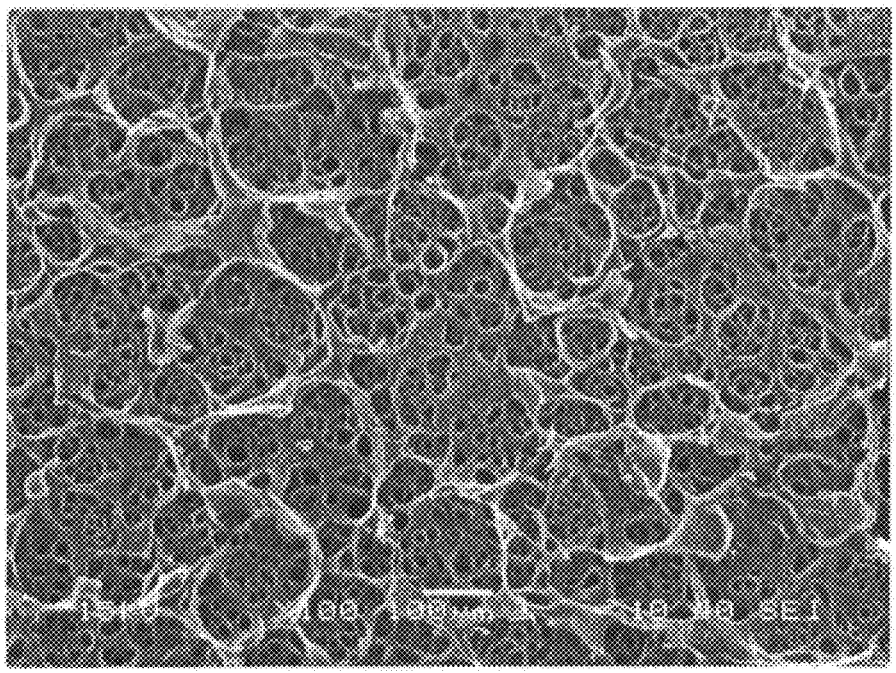
FIGS. 10A and 10B (also referred herein as FIGS. 10(a) and 10(b), respectively) are photographs of the surface of the article with the foamed surface prepared in Working Example 7, obtained with a scanning electron microscope.

The surface of the prepared article was observed with a scanning electron microscope. An image obtained at 100 magnifications is shown in FIG. 10(a), and an image at 3000 magnifications in FIG. 10(b). As shown in FIG. 10(a), many open pores and many passages formed in the inner walls of the open pores were observed in the surface of the article, in the same manner as with the article with the foamed surface obtained in Working Example 5. The number of passages was essentially the same as that of passages in the article with the foamed surface obtained in Working Example 6. Large open pores originating from large pores had a diameter ranging from 30 to 300 µm, which was essentially the same as the diameter of the large open pores included in the article of Working Example 6. The reason that the diameter of the large open pores and the number of passages were essentially the same as the corresponding values in Working Example 6 is considered to be that the coagulation of the foamed base was almost completed after the foamed base was immersed in the 63% aqueous solution of sulfuric acid for ten minutes.

Figure 10B:
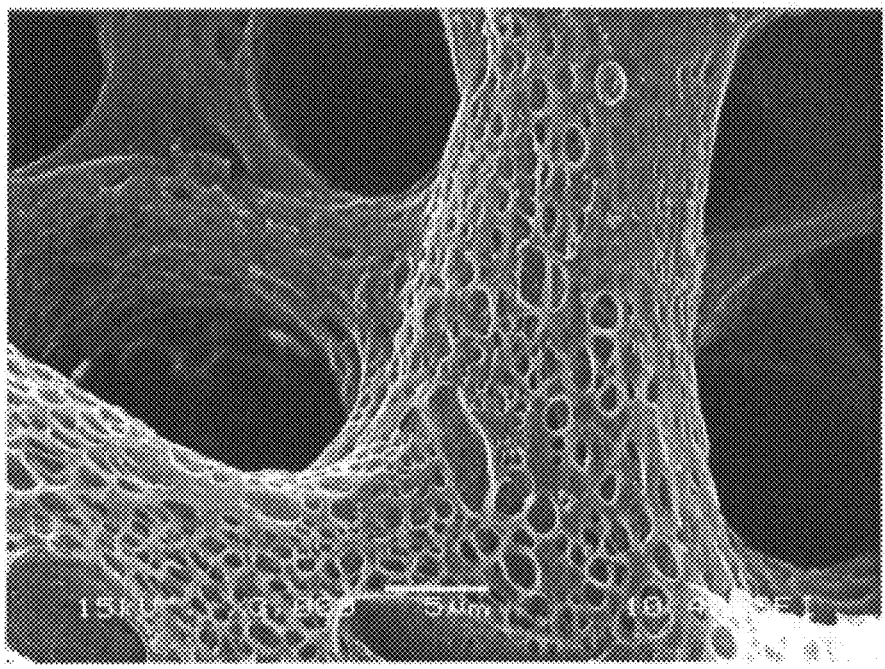

As shown in FIG. 10(b), small open pores originating from small pores had a diameter ranging from 0.5 to 5 µm.

The average diameter of the small open pores and that of the large open pores were calculated with the same method as in Working Example 1: The former was 1.8 µm, and the latter was 122 µm.

The proportion of the area of the large open pores to that of the entire photograph was calculated with the same method as in Working Example 1, and it was 68%.

Working Example 8

An article with a foamed surface was obtained with the same method as in Working Example 5, except that an aqueous solution of sulfuric acid with a concentration of 86% was used in place of the 63% aqueous solution of sulfuric acid.

Figure 11A:
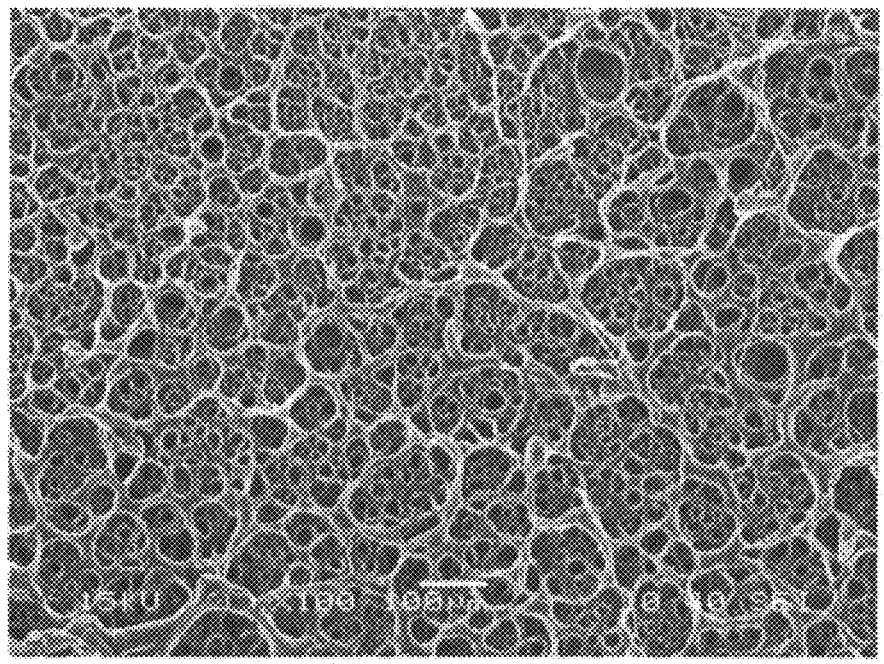
FIGS. 11A and 11B (also referred herein as FIGS. 11(a) and 11(b), respectively) are photographs of the surface of the article with the foamed surface prepared in Working Example 8, obtained with a scanning electron microscope.

The surface of the prepared article was observed with a scanning electron microscope. An image obtained at 100 magnifications is shown in FIG. 11(a), and an image at 3000 magnifications in FIG. 11(b). As shown in FIG. 11(a), many open pores and many passages formed in the inner walls of the open pores were observed in the surface of the surface foamed article, in the same manner as with the article with the foamed surface obtained in Working Example 5. Large-diameter passages, formed by the connection of a large open pore with large pores, had a larger diameter than the equivalents in the article obtained in Working Example 5. The diameter ranged from 10 to 20 µm. Large open pores originating from large pores had a larger diameter than the large open pores included in the article with the foamed surface of Working Example 5, and the diameter ranged from 50 to 180 µm.

Figure 11B:
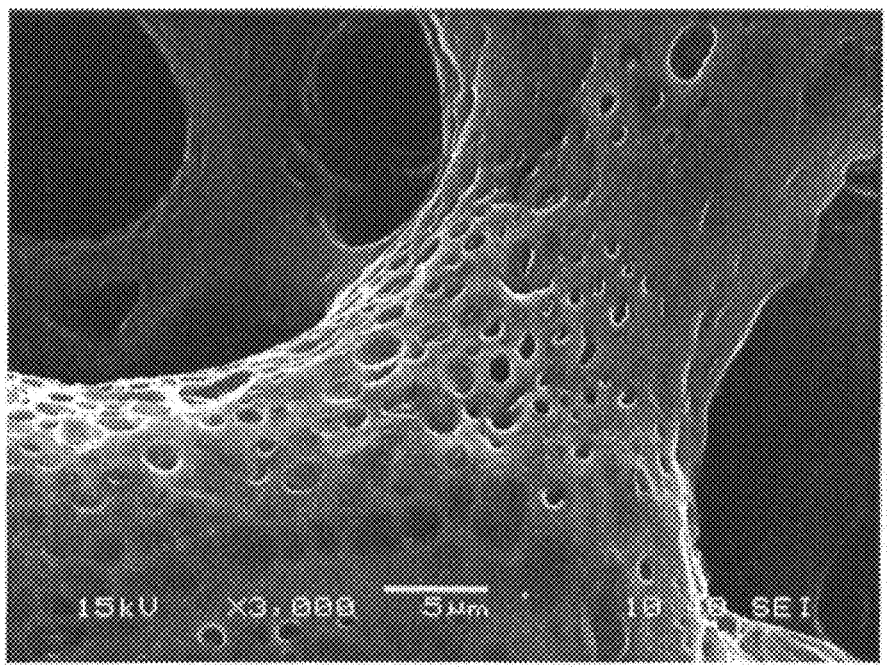

As shown in FIG. 11(b), small open pores originating from small pores had a diameter ranging from 0.3 to 4 µm.

The average diameter of the small open pores and that of the large open pores were calculated with the same method as in Working Example 1: The former was 0.8 µm, and the latter was 97 µm.

The proportion of the area of the large open pores to that of the entire photograph was calculated with the same method as in Working Example 1, and it was 67%.

Working Example 9

An article with a foamed surface was obtained with the same method as in Working Example 6, except that an aqueous solution of sulfuric acid with a concentration of 86% was used in place of the 63% aqueous solution of sulfuric acid.

Figure 12A:
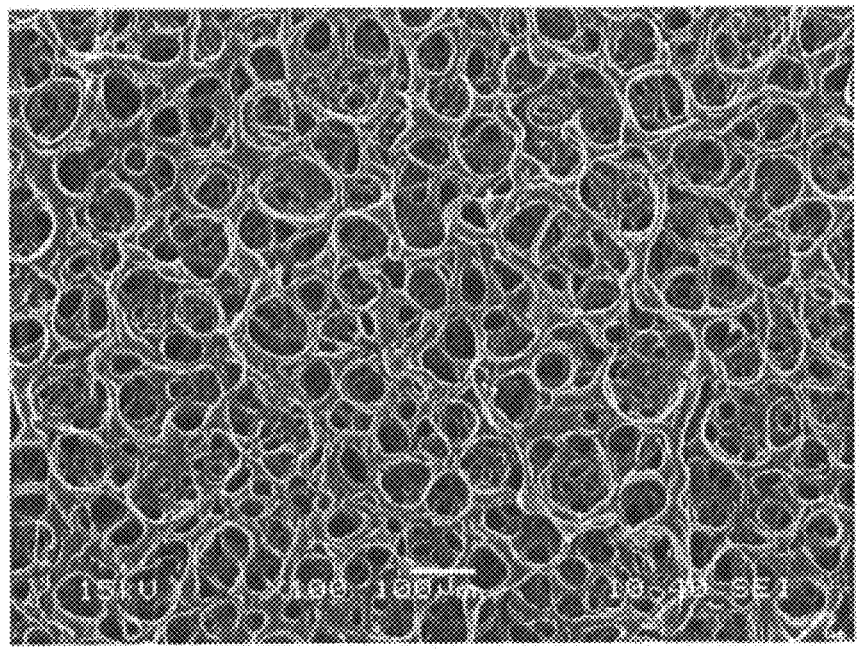
FIGS. 12A and 12B (also referred herein as FIGS. 12(*a*) and 12(*b*), respectively) are photographs of the surface of the article with the foamed surface prepared in Working Example 9, obtained with a scanning electron microscope.

The surface of the prepared article was observed with a scanning electron microscope. An image obtained at 100 magnifications is shown in FIG. 12(a), and an image at 3000 magnifications in FIG. 12(b). As shown in FIG. 12(a), many open pores and many passages formed in the inner walls of the open pores were observed in the surface of the surface foamed article, in the same manner as with the article with the foamed surface obtained in Working Example 5. Large-diameter passages, formed by the connection of a large open pore with large pores, had a markedly larger diameter than the equivalents in the article obtained in Working Example 8 had: The diameter ranged from 20 to 40 µm. The number of large-diameter passages was less than that of the equivalents in Working Example 8. Large open pores originating from large pores had a diameter which was essentially the same as the diameter of the large open pores included in the article with the foamed surface of Working Example 8, and the diameter ranged from 60 to 170 µm.

Figure 12B:
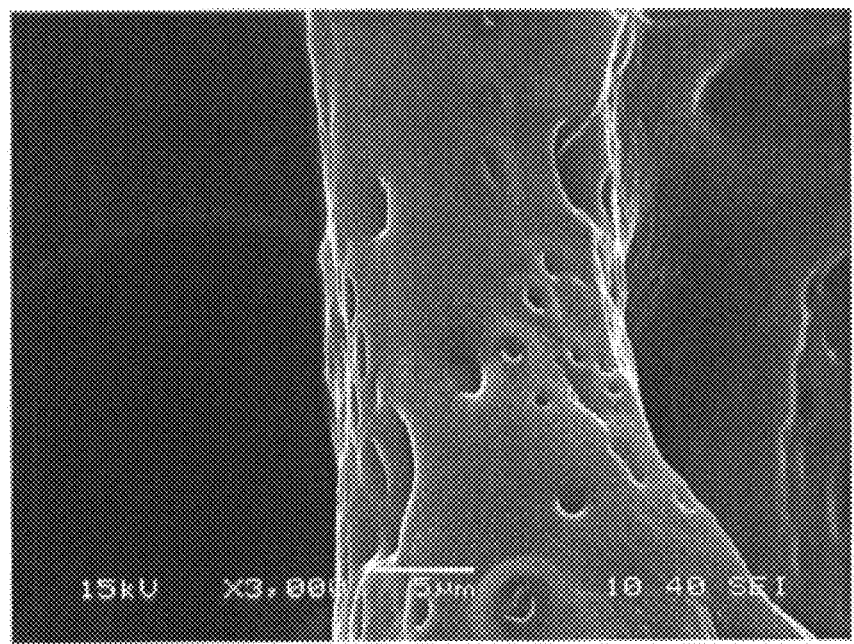

As shown in FIG. 12(b), small open pores originating from small pores had a diameter ranging from 0.5 to 1 µm.

The average diameter of the small open pores and that of the large open pores were calculated with the same method as in Working Example 1: The former was 0.6 µm, and the latter was 92 µm.

Figure 13:
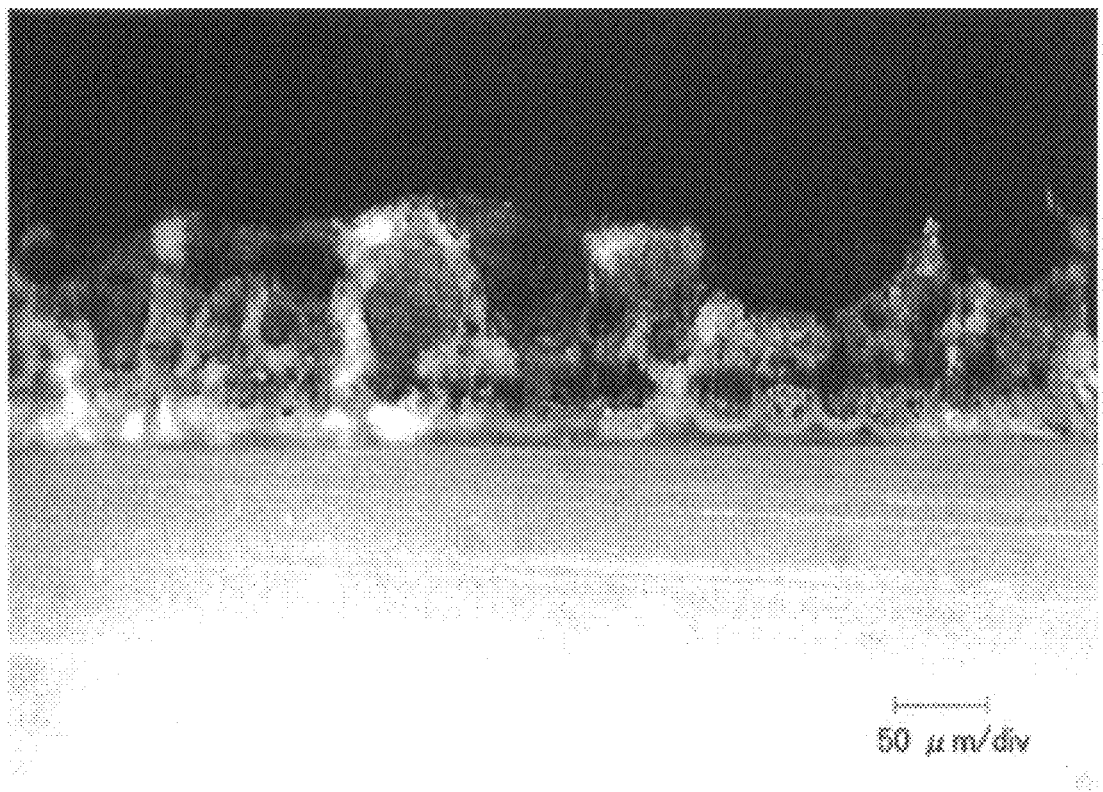
FIG. 13 is a photograph of a section of the article with the foamed surface prepared in Working Example 9, obtained with a scanning electron microscope.

A vertical section of the prepared article was observed through a microscope at 500 magnifications. An obtained image is shown in FIG. 13. Large pores with a diameter from 30 to 50 µm were observed in the entire superficial layer with a thickness of about 120 µm, extending inwards from the surface of a test piece of the superficial layer.

The proportion of the area of the large open pores to that of the entire photograph was calculated with the same method as in Working Example 1, and it was 65%.

Working Example 10

An article with a foamed surface was obtained with the same method as in Working Example 7, except that an aqueous solution of sulfuric acid with a concentration of 86% was used in place of the 63% aqueous solution of sulfuric acid.

Figure 14A:
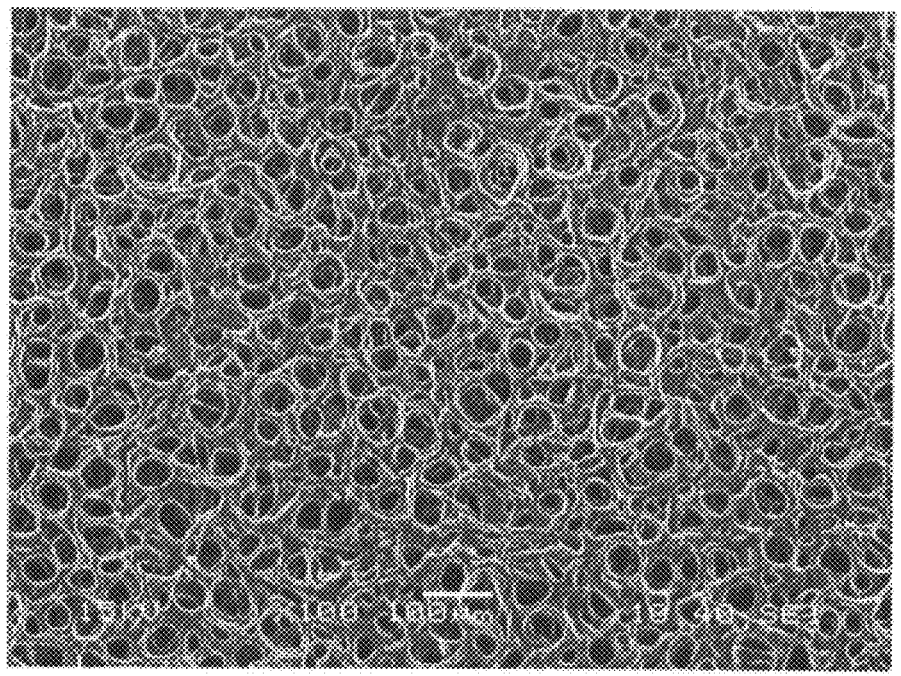
FIGS. 14A and 14B (also referred herein as FIGS. 14(*a*) and 14(*b*), respectively) are photographs of the surface of the article with the foamed surface prepared in Working Example 10, obtained with a scanning electron microscope.

The surface of the prepared article was observed with a scanning electron microscope. An image obtained at 100 magnifications is shown in FIG. 14(a), and an image at 3000 magnifications in FIG. 14(b). As shown in FIG. 14(a), many open pores and many passages formed in the inner walls of the open pores were observed in the surface of the surface foamed article, in the same manner as with the article obtained in Working Example 5. Large-diameter passages, formed by the connection of a large open pore with large pores, had a diameter which was essentially the same as the diameter of the large-diameter passages in the article obtained in Working Example 9. The diameter ranged from 20 to 40 µm. Large open pores originating from large pores had a smaller diameter than the equivalents in the article obtained in Working Example 9 had, and the diameter ranged from 30 to 80 µm.

Figure 14B:
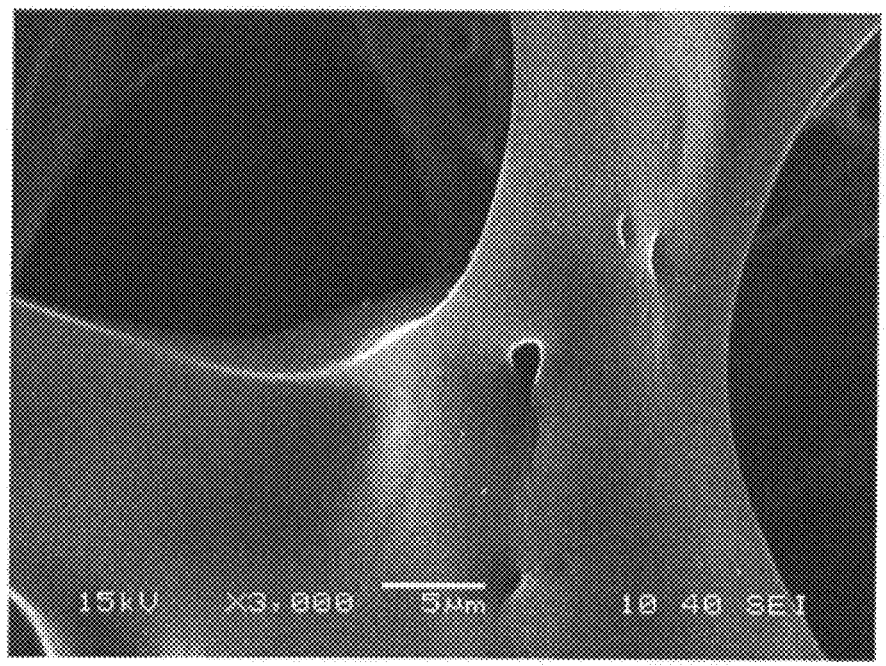

As shown in FIG. 14(b), small open pores originating from small pores had a diameter ranging from 0.2 to 1 µm.

The average diameter of the small open pores and that of the large open pores were calculated with the same method as in Working Example 1: The former was 0.6 µm, and the latter was 42 µm.

The proportion of the area of the large open pores to that of the entire photograph was calculated with the same method as in Working Example 1, and it was 54%.

Preparation and Evaluation of Implant with Bioactive Substance

Working Example 11

The article with the foamed surface prepared in Working Example 1 was immersed in an aqueous solution of calcium chloride with a calcium-ion concentration of 2 M for 60 minutes, and subsequently in an aqueous solution of dipotassium hydrogen phosphate with a phosphate-ion concentration of 2 M for 60 minutes. A solution-immersed base was thus obtained.

Then the solution-immerse base was further immersed in pure water for three hours, which was followed by washing of the base in pure water for ten minutes while the pure water was being irradiated with ultrasound. Subsequently the washed base was dried at 120° C. for three hours. An implant with a bioactive substance was obtained.

Figure 15:
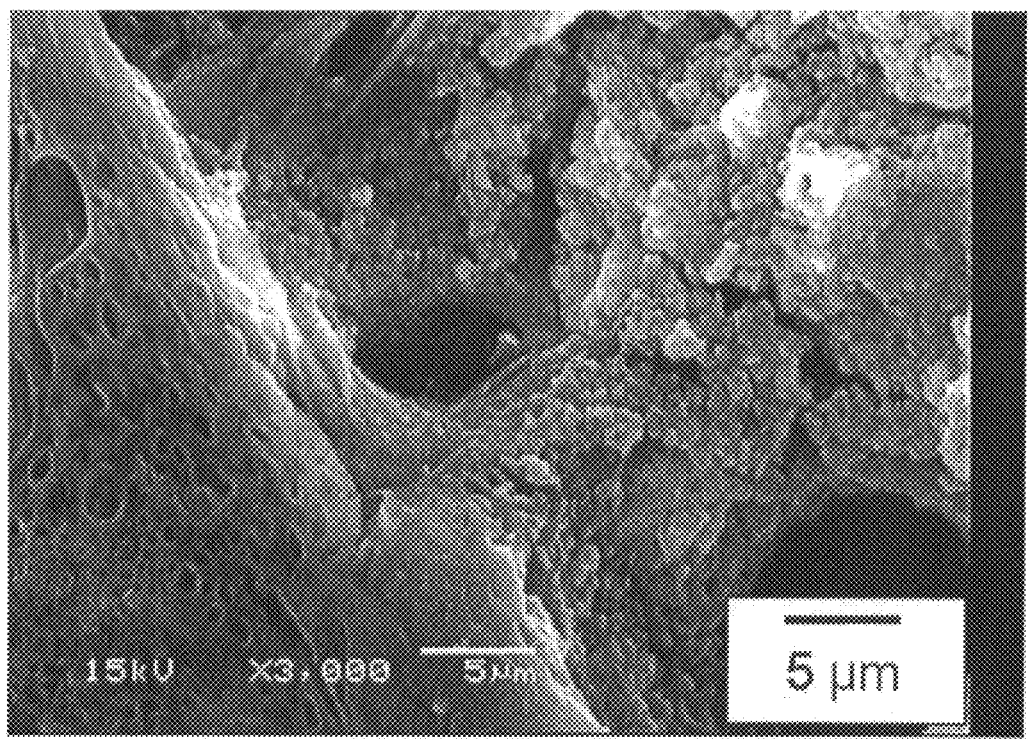
FIG. 15 is a photograph of the surface of the implant with a bioactive substance prepared in Working Example 11, obtained with a scanning electron microscope.

The surface of the implant was observed through a scanning electron microscope with 3000 magnifications. An image of the surface is shown in FIG. 15. On the surface and the inner walls of open pores formed in the surface were observed particles adhering thereto, the particles precipitating from the aqueous solutions of calcium chloride and dipotassium hydrogen phosphate in which the article had been immersed. These particles were analyzed with an X-ray diffractometer. As a result, peaks belonging to hydroxyapatite were observed. These peaks were broad, which indicated that hydroxyapatite with low crystallinity was produced.

A photograph taken with a scanning electron microscope of the surface of the implant was made binary with an image processing software ("Scion Image" produced by Scion Corporation), or into portions with the particles of hydroxyapatite and other portions. The proportion of the area of the portions with hydroxyapatite particles on the surface of the implant or the inner walls of open pores formed in the surface thereof, to the area of the entire photograph was calculated. The proportion was 23%.

| EXPLANATION OF REFERENCE NUMERALS | |
|---|---|
| 1 | article with a foamed surface |
| 2, 202a, 202b | body |
| 3, 203a, 203b | small pore |
| 4, 204a, 204b | large pores |
| 5, 205a, 205b | superficial layer |
| 6, 206a, 206b | open pore |
| 7, 207a, 207b | passage |
| 8 | isolated pore |
| 9 | connected pore |
| 13, 213a, 213b | small open pore |
| 14, 214a, 214b | large open pore |
| 15 | small-diameter passage |
| 16, 216a, 216b | large-diameter passage |
| 210a, 210b | bioactive substance |
| 211a, 211b | inner wall |
| 212a, 212b | implant |
| A | average diameter of the small pores |
| B | average diameter of the large pores |
| C | diameter of the small-diameter passage |
| D | diameter of the large-diameter passage |

We claim:

1. A method of producing an article with a foamed surface comprising:
   a step 1 of forming small pores in a surface of a base made of a plastic to produce a base with small pores;
   a step 2 of immersing the base with small pores, obtained in step 1, in a solution including a foaming agent to prepare a foaming agent-including base;
   a step 3 of immersing the foaming agent-including base, obtained in step 2, in a foaming solution that makes the plastic swell and the foaming agent foam to prepare a foamed base; and
   a step 4 of immersing the foamed base, obtained in step 3, in a coagulating solution that coagulates the swollen plastic.

2. The method as according to claim 1, further comprising applying the article with the foamed surface to an implant.

3. The method according to claim 1, wherein the plastic is an engineering plastic.

4. The method according to claim 1, wherein the plastic is polyetheretherketone.

5. The method according to claim 1, wherein the plastic includes at least one fiber selected from the group consisting of carbon fiber, glass fiber, ceramic fiber, metal fiber and organic fiber.

6. The method according to claim 1, wherein the foaming solution used in step 3 is concentrated sulfuric acid.

7. The method according to claim 1, wherein a porous structure formed in a superficial layer of the foamed article is controlled by changing at least one of a kind of the coagulating solution, a concentration of the coagulating solution and a time period for which the foamed base is immersed in the coagulating solution.

8. The method according to claim 1, wherein the coagulating solution is at least one selected from the group consisting of water and a slow coagulating solution which takes a longer time to coagulate the swollen plastic than water.

9. The method according to claim 8, wherein the slow coagulating solution is a solution of sulfuric acid with a concentration of less than 90%.

10. The method according to claim 1, wherein the foaming agent is a carbonate.

11. The method according to claim 10, wherein the carbonate includes at least one carbonate compound selected from the group consisting of sodium hydrogen carbonate, sodium carbonate and potassium carbonate.

12. A method of producing an implant comprising immersing an article with a foamed surface, prepared by the method according to claim 1, both in a first solution including calcium ions and a second solution including phosphate ions wherein the article may be first immersed in either of the first and second solutions.

\* \* \* \* \*